(12) United States Patent
Smutney et al.

(10) Patent No.: US 6,733,465 B1
(45) Date of Patent: *May 11, 2004

(54) HOLDER FOR BLOOD COLLECTION NEEDLE WITH BLUNTING MECHANISM

(75) Inventors: Chad C. Smutney, Stafford Springs, CT (US); John M. Polidoro, Coventry, CT (US); Marius Walter Hauri, Putnam, CT (US); P. Spencer Kinsey, Newington, CT (US); Richard G. Holdaway, Storrs, CT (US); Carl R. Sahi, Coventry, CT (US)

(73) Assignee: Bio-Plexus, Inc., Vernon, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/649,773

(22) Filed: Aug. 29, 2000

Related U.S. Application Data

(63) Continuation-in-part of application No. 09/199,742, filed on Nov. 25, 1998, now Pat. No. 6,146,337.
(60) Provisional application No. 60/211,897, filed on Jun. 16, 2000.

(51) Int. Cl.⁷ .............................. A61B 5/00; B65D 81/00
(52) U.S. Cl. ....................................................... 600/576
(58) Field of Search .................................. 600/576, 573, 600/577; 604/170, 158, 198, 110, 51

(56) References Cited

U.S. PATENT DOCUMENTS

| | | |
|---|---|---|
| 1,527,291 A | 2/1925 | Zorraquin |
| 2,623,520 A | 12/1952 | Bamford, Jr. et al. ...... 128/221 |
| 2,623,521 A | 12/1952 | Shaw ........................ 128/221 |
| 3,840,008 A | 10/1974 | Noiles ....................... 128/221 |
| 3,923,066 A | 12/1975 | Francisoud et al. ......... 128/348 |
| 4,535,773 A | 8/1985 | Yoon ............................ 604/51 |
| 4,613,329 A | 9/1986 | Bodicky .................... 604/158 |
| 4,664,654 A | 5/1987 | Strauss ...................... 604/198 |
| 4,675,005 A | 6/1987 | DeLuccia ................... 604/110 |
| 4,747,831 A | 5/1988 | Kulli ......................... 604/110 |
| 4,778,453 A | 10/1988 | Lopez ........................ 604/110 |
| 4,790,828 A | 12/1988 | Dombrowski et al. ...... 604/198 |
| 4,795,432 A | 1/1989 | Karczmer ................... 604/110 |
| 4,804,371 A | 2/1989 | Vaillancourt ............... 604/198 |
| 4,808,168 A | 2/1989 | Warring ..................... 604/158 |
| 4,813,426 A | 3/1989 | Haber et al. ................ 128/763 |
| 4,869,717 A | 9/1989 | Adair .......................... 604/51 |
| 4,978,344 A | 12/1990 | Dombrowski et al. ...... 604/198 |
| 5,009,642 A | 4/1991 | Sahi .......................... 604/158 |
| 5,030,208 A | 7/1991 | Novacek et al. ............ 604/195 |
| 5,098,402 A | 3/1992 | Davis ........................ 604/195 |
| 5,104,381 A | 4/1992 | Gresl et al. ................. 604/164 |

(List continued on next page.)

FOREIGN PATENT DOCUMENTS

| | | | |
|---|---|---|---|
| DE | 2 147 183 | 4/1973 | .......... A61M/5/18 |
| EP | 0 405 883 A2 | 1/1991 | .......... A61B/17/34 |
| GB | 802351 | 10/1958 | |

*Primary Examiner*—Max F. Hindenburg
*Assistant Examiner*—Brian Szmal
(74) *Attorney, Agent, or Firm*—Knobbe, Martens, Olson & Bear, LLP

(57) ABSTRACT

The present invention relates to a blood collection system comprising a blood collection tube, a tube holder, and a self-blunting blood collection needle. A blunting member is deployed upon withdrawal of a blood collection tube from the tube holder, to blunt the needle and so safeguard the patient and the technician from inadvertent needle sticks. The blunting member is retracted to re-sharpen the needle when a subsequent collection tube is inserted into the holder. The mechanism effects blunting and re-sharpening of the needle with requiring that the technician manipulate the mechanism in a manner different from that of conventional, non-blunting blood collection needles. Four types of mechanisms are disclosed: a rack and pinion mechanism; a cylindrical cam mechanism; lever mechanisms and a reversing strap mechanism.

17 Claims, 20 Drawing Sheets

U.S. PATENT DOCUMENTS

| | | | |
|---|---|---|---|
| 5,104,382 A | 4/1992 | Brinkerhoff et al. | 604/165 |
| 5,139,485 A | 8/1992 | Smith et al. | 604/158 |
| 5,190,050 A | 3/1993 | Nitsche | 128/772 |
| 5,201,710 A | 4/1993 | Caselli | 604/110 |
| 5,226,426 A | 7/1993 | Yoon | 128/753 |
| 5,256,148 A | 10/1993 | Smith et al. | 604/158 |
| 5,330,432 A | 7/1994 | Yoon | 604/164 |
| 5,334,159 A | 8/1994 | Turkel | 604/158 |
| 5,336,176 A | 8/1994 | Yoon | 604/51 |
| 5,364,365 A | 11/1994 | Wortrich | 604/158 |
| 5,374,252 A | 12/1994 | Banks et al. | 604/158 |
| 5,423,760 A | 6/1995 | Yoon | 604/165 |
| 5,423,770 A | 6/1995 | Yoon | 604/281 |
| 5,476,106 A | 12/1995 | Gartz | 128/898 |
| 5,478,317 A | 12/1995 | Yoon | 604/165 |
| 5,549,564 A | 8/1996 | Yoon | 604/165 |
| 5,562,629 A | 10/1996 | Haughton et al. | 604/158 |
| 5,586,991 A | 12/1996 | Yoon | 606/185 |
| 5,634,934 A | 6/1997 | Yoon | 606/185 |
| 5,645,556 A | 7/1997 | Yoon | 606/185 |
| 5,665,072 A | 9/1997 | Yoon | 604/164 |
| 5,718,239 A | 2/1998 | Newby et al. | 128/763 |
| 5,779,680 A | 7/1998 | Yoon | 604/164 |
| 5,951,520 A | 9/1999 | Burzynski et al. | 604/170 |
| 6,146,337 A * | 11/2000 | Polidoro et al. | 600/576 |

* cited by examiner

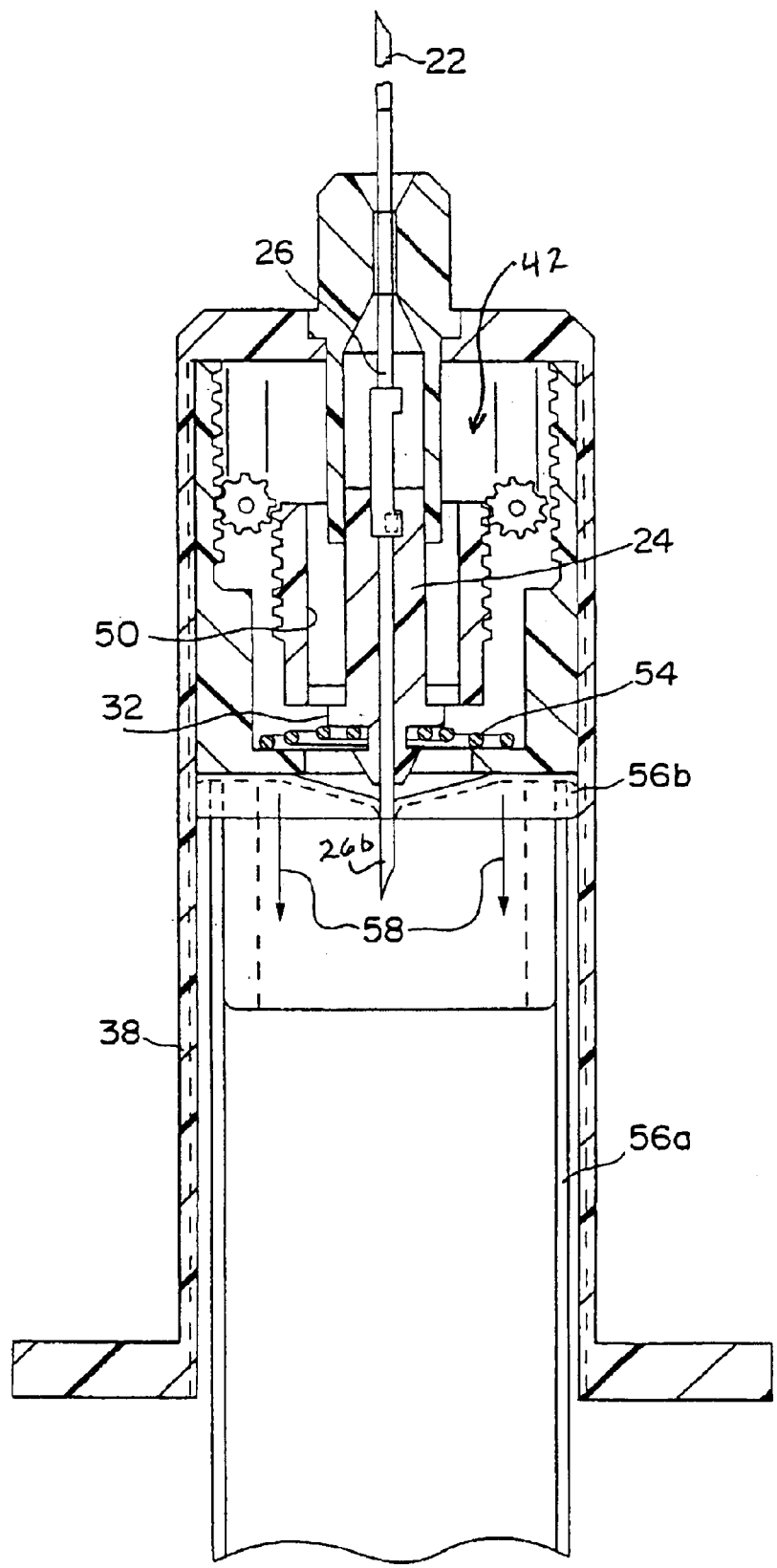
F I G. 4A

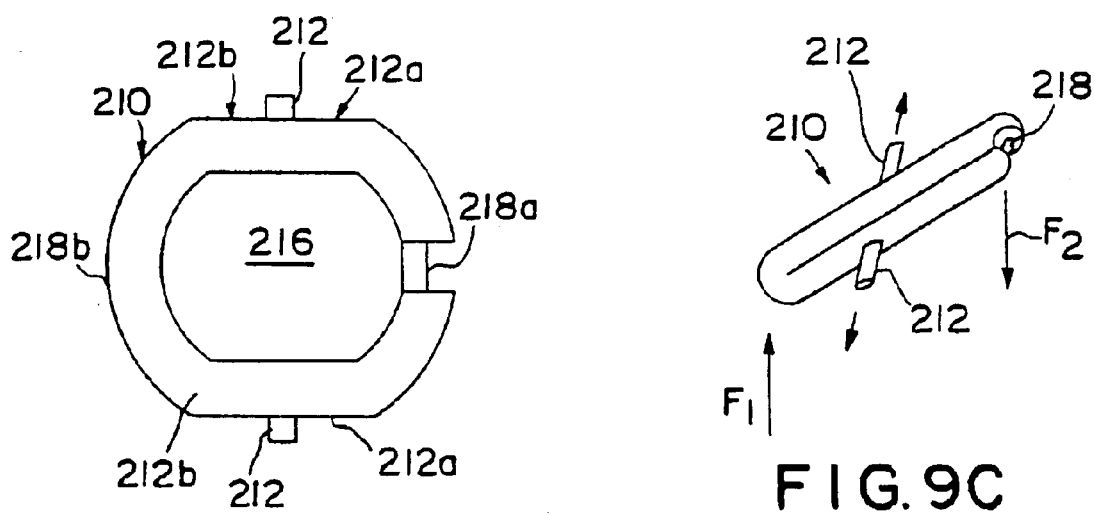
FIG. 9B
FIG. 9C
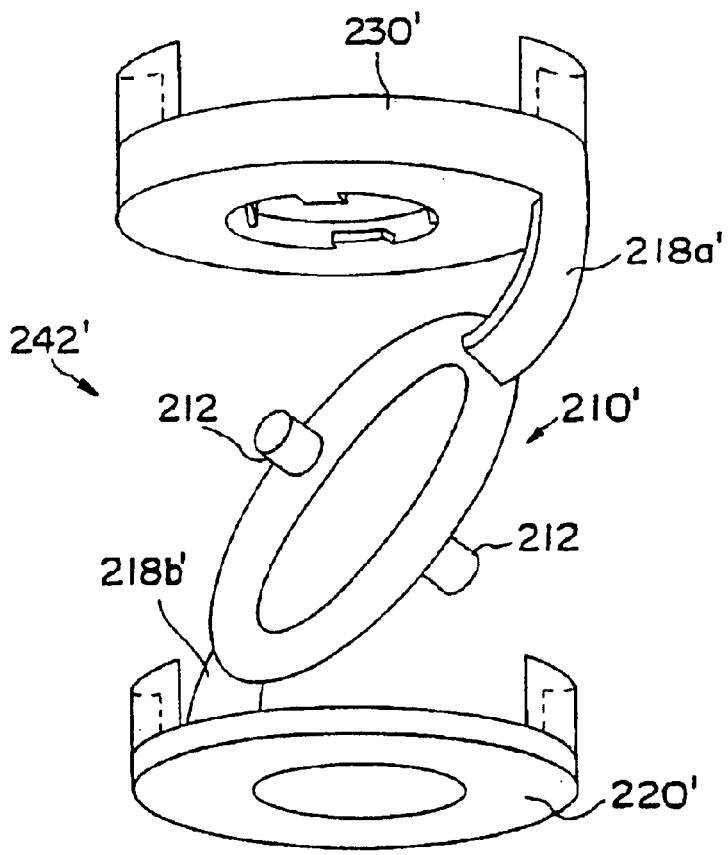
FIG. 9D

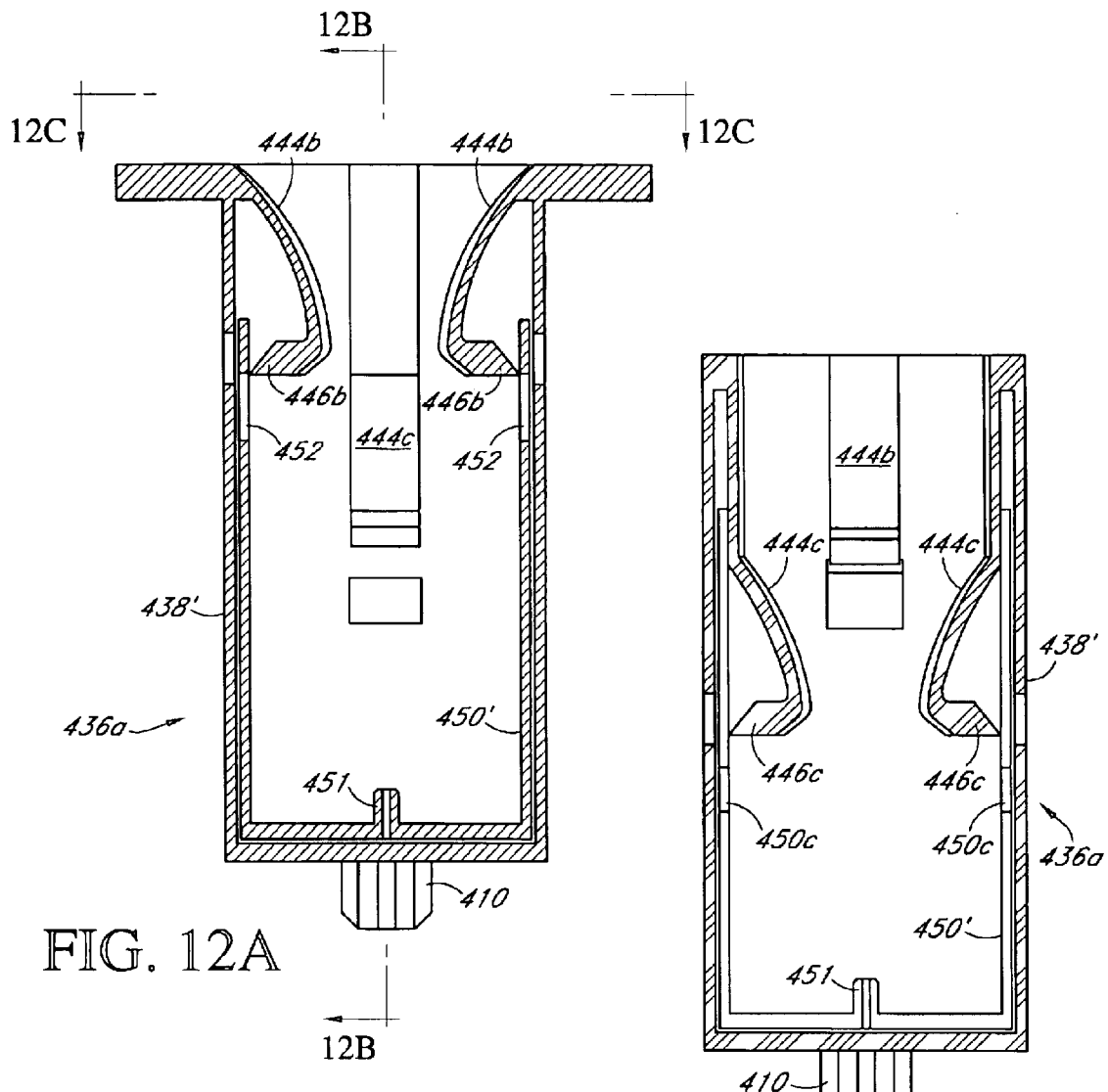
FIG. 12A
FIG. 12B
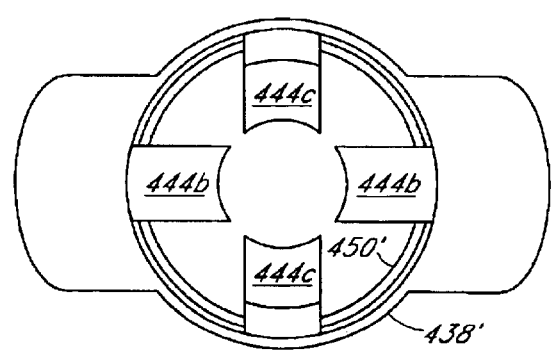
FIG. 12C

HOLDER FOR BLOOD COLLECTION NEEDLE WITH BLUNTING MECHANISM

CROSS REFERENCE TO RELATED APPLICATION

This application is a continuation-in-part of application Ser. No. 09/199,742, filed Nov. 25, 1998 now U.S. Pat. No. 6,146,337, and this application claims the benefit of U.S. provisional application No. 60/211,897, filed Jun. 16, 2000.

BACKGROUND OF THE INVENTION

Field of the Invention

The present invention pertains to self-blunting needle devices and, in particular, to holders for blood collection needles.

Conventional blood collection systems are known in the art to comprise a holder, typically in the form of a generally cylindrical shell, that holds a double-ended needle cannula. One end of the needle cannula extends forward from the holder and is used for venipuncture (the "venipuncture needle") while the other end (the "filling needle") extends into the holder and is used to puncture the seal cap on a sample fluid collection tube (which, typically, is vacuum-sealed). The device is used by unsheathing the venipuncture needle and effecting venipuncture and then inserting the sealed end of a collection tube into the holder and pushing the seal cap against the boot that covers the tip of the filling needle. The filling needle pierces the boot and the seal cap and blood is drawn into the collection tube. If additional samples are required, the first collection tube is removed and a second collection tube is pushed into the holder in its place. When the last tube is filled, the blood collection needle is withdrawn from the patient's vein.

Prior art self-blunting blood collection needles have provided a deployable, locking, blunting member to protect the user against inadvertent needle sticks but required the user to engage in an extraneous manipulation of the sample tube in order to deploy the blunting member such as the insertion of the sample tube past a discernible "stop" point at which the collection tube is already fully engaged by the filling needle. There is need, therefore, for a self-blunting needle mechanism that does not require manipulation beyond that which is familiar to medical technicians with the use of conventional blood collection needles.

SUMMARY OF THE INVENTION

The present invention relates to a needle holder apparatus comprising a shell dimensioned and configured for receiving and holding a sample collection tube therein and for carrying thereon a needle cannula, an actuator movably disposed in the shell for engaging and moving a blunting member longitudinally within the shell and means for moving the actuator between a forward position and a retracted position in response to the insertion and withdrawal of a sample collection tube in the shell.

According to one aspect of the invention, the means for moving the actuator may comprise a transmitter device connected to the shell and being configured to move obliquely in the shell upon insertion of such sample collection tube into the shell. There may also be a linkage between the transmitter device and the actuator to convert the oblique motion of the transmitter device into rearward motion of the actuator when such sample tube is inserted into the apparatus. The apparatus may include a biasing member positioned and configured to urge the actuator toward the forward position.

In one species of the invention, the linkage may comprise a cam and follower engagement between the actuator and the transmitter device. Optionally, there may be a staggered cam and follower engagement between the actuator and the transmitter device.

According to yet another aspect of the invention, the transmitter device may be configured to contact such sample collection tube at a point between the connection to the shell and the linkage to the actuator.

According to yet another aspect of the invention, the transmitter device may extend forwardly in the shell from its point of attachment to the shell.

According to still another embodiment of the invention, the transmitter device may comprise at least two transmitter arms.

According to another aspect of the invention, either of the actuator and the transmitter device may comprise a cam surface.

The apparatus may comprise a biasing member urging the actuator member toward the forward position.

In a particular embodiment, this invention may provide a needle holder apparatus comprising a shell dimensioned and configured for receiving and holding a sample collection tube therein and for carrying thereon a needle cannula, an actuator movably disposed in the shell for engaging and moving a blunting member axially within the shell, a transmitter device connected to the shell and being configured to contact a sample collection tube which may be inserted into the shell and to move obliquely relative to the motion of the sample collection tube, and a positive motion cam engagement between the transmitter device and the actuator to convert the oblique motion of the transmitter device into axial motion of the actuator, to move the actuator axially in the shell in response to the oblique motion of the transmitter device, wherein the apparatus is biased to dispose the actuator in the forward position.

The present invention also provides a blood collection needle comprising a shell dimensioned and configured for receiving and holding a sample collection tube therein, a needle cannula carried on the shell, a blunting member disposed telescopically within the needle cannula for movement between a withdrawn position which disposes the needle in a sharpened configuration and a blunting position which disposes the needle in a blunted configuration, and a mechanism for moving the blunting member to the withdrawn position when a sample collection tube is inserted into the holder and for moving the blunting member to the blunting position when the sample collection tube is withdrawn from the shell.

In a particular embodiment, the mechanism may comprise an actuator movably disposed in the shell, the actuator being secured to the blunting member so that the blunting member can be moved between the blunting position and the withdrawn position by movement of the actuator, a movable transmitter device connected to the shell and being configured for contact with a sample collection tube which may be inserted into the shell and to move obliquely relative to the motion of a sample collection tube in the shell, a biasing member configured to urge the blunting member to the blunting position upon withdrawal of a sample collection tube from the shell, and a linkage between the transmitter device and the actuator to convert the oblique motion of the transmitter device into forward and rearward motion of the actuator, to move the blunting member from the blunting position to the withdrawn position.

Further details concerning the invention are described below with reference to the appended Figures.

BRIEF DESCRIPTION OF THE DRAWINGS

FIGS. 4A and 4B are views similar to FIG. 3 of the device of FIG. 3 in the insertion and blunted configurations, respectively;

FIG. 9B is a plan view of ring lever 210 of FIG. 9A;

FIG. 9C is a perspective view of the ring lever 210 of FIG. 9B;

FIG. 9D is a perspective view of an alternative embodiment of a lever-type mechanism similar to the one of FIGS. 9A–9C;

FIGS. 12A and 12B are cross-sectional views of a holder for a blood collection needle in accordance with another embodiment of the invention;

FIG. 12C is an end view of the embodiment of FIGS. 12A and 12B;

DETAILED DESCRIPTION OF THE INVENTION AND PREFERRED EMBODIMENTS THEREOF

Figure 1A:
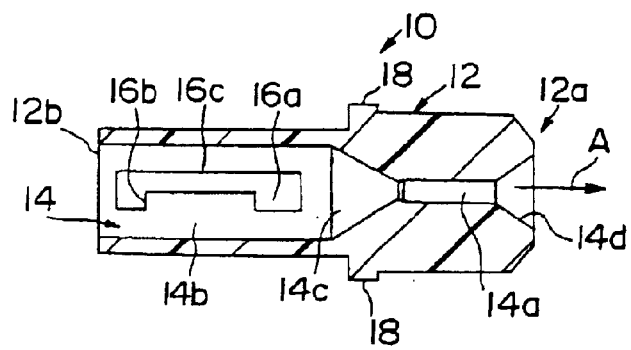
FIG. 1A is a cross-sectional view of a needle hub for holding a needle cannula in a blood collection device.

The present invention relates to a holder for a blood collection needle having a movable blunting member. The holder has a mechanism for engaging and deploying a blunting member upon withdrawal of a blood collection tube from the tube holder, to blunt the venipuncture needle and so safeguard the patient and the technician from inadvertent needle sticks. The mechanism may function to retract the blunting member to re-sharpen the venipuncture needle when a subsequent collection tube is inserted into the holder. The mechanism is responsive to the insertion and withdrawal of the blood collection tube to retract and deploy the blunting member accordingly. One basic and novel feature of the present invention is that the mechanism allows the user to blunt and, optionally, re-sharpen the venipuncture needle without requiring manipulation of the collection tube or the needle holder other than that normally performed for conventional blood collection needle systems, as described above. For example, it is not necessary to manipulate the blunting member in any manner other than by the insertion or withdrawal of the sample tube to engage or disengage the filling needle. Four types of mechanisms are disclosed: a rack and pinion mechanism, a cylindrical cam mechanism, lever mechanisms, and a pliable, resilient strap mechanism. Generally, the mechanism in each of these devices comprises an actuator member which engages the blunting member for movement in the holder between a forward or deployed position which places the device in a blunted configuration and a rearward or withdrawn position which places the device in a sharpened configuration. The mechanism also comprises a transmitter which is moved by a sample collection tube as the tube is inserted into or removed from the device. The mechanism is designed to convert motion imposed on the transmitter device upon insertion of a sample collection tube as it is inserted into the device into a rearward motion of the actuator and consequently into withdrawal of a blunting member, if one is secured to the actuator.

In some embodiments the transmitter moves forward or rearward in the device with the sample collection tube and the mechanism includes a reversing member for imparting a motion on the actuator in a direction opposite to that of the transmitter device. In other embodiments, the mechanism includes a cam and follower engagement between the transmitter and the actuator. In another embodiment, the transmitter moves obliquely relative to the sample collection tube.

Also disclosed is an optional safety needle assembly comprising a needle cannula mounted in a needle hub combined with a blunting member mounted in a shuttle. The blunting member is designed to be received within the needle cannula and the shuttle is configured to be received within the needle hub. A locking mechanism comprising a detent resiliently mounted on the shuttle is configured to releasably engage locking apertures in the needle hub. The locking mechanism and the blunting mechanism may be used together by configuring the blunting mechanisms to release the detent from the locking apertures when the needle assembly is installed in the needle holder.

FIG. 1A shows a needle hub 10 that comprises a generally cylindrical body 12 having a longitudinal axis A, a first end 12a and a second end 12b. Needle hub 10 also comprises a circumferential locking flange 18 and at least one locking spline 20 (FIG. 1D) by which needle hub 10 can be secured in a needle holder, as described below. The interior of needle hub 10 comprises a hub passageway 14 extending therethrough. The shuttle portion 14b of passageway 14 (generally between second end 12b and flange 18) is dimensioned and configured to slidably receive a shuttle (FIG. 1B) therein. Body 12 defines two locking notches 16a and 16b and a channel 16c formed together as an aperture through the cylindrical wall of body 12. The mounting portion 14a of passageway 14 (generally between flange 18 and first end 12a) is dimensioned and configured to receive a needle cannula in the forward end thereof. The funnel-like insertion regions 14c and 14d at the ends of mounting portion 14a of passageway 14 converge from the shuttle portion 14b and the first end of hub 10, respectively, and facilitate the insertion therein of a blunting member and a needle cannula in assembly steps described below.

Figure 1B:
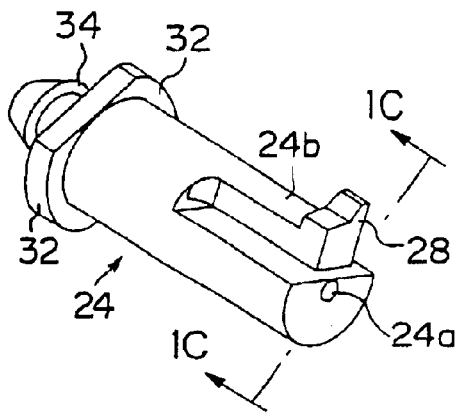
FIG. 1B is a perspective view of a blunting member shuttle intended for use with the needle hub of FIG. 1A.
Figure 1C:
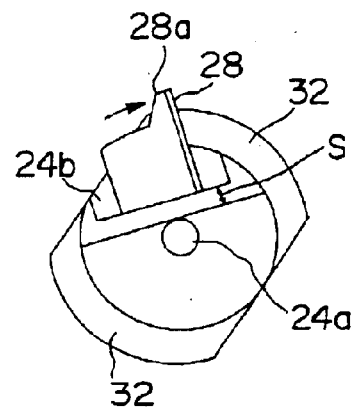
FIG. 1C is a view of the shuttle of FIG. 1B taken along line 1C—1C.

FIG. 1B shows a blunting member shuttle 24 which has a generally cylindrical body that is dimensioned and configured to be slidably received within the shuttle portion 14b of passageway 14 of hub 10, as will be described below. Shuttle 24 defines a central axial passageway 24a therethrough within which may be mounted a blunting member. Shuttle 24 comprises a detent 28 that is mounted on the end of a resilient arm 24b. Resilient arm 24b suspends detent 28 at a stand-off from the remainder of the shuttle body, indicated as stand-off S in the end view of FIG. 1C. As is evident from FIG. 1C, detent 28 has a protruding surface 28a that is disposed obliquely relative to the cylindrical periphery of shuttle 24. Therefore, a force applied upon surface 28a substantially along a tangent to the shuttle body (or parallel to such a tangent) can drive detent 28 in a radial direction (towards passageway 24a), narrowing stand-off S by flexing arm 24b.

Shuttle 24 comprises shuttle flanges 32 that permit shuttle 24 to engage another structure, as described below. Shuttle 24 also defines a boot barb 34 on which a self-sealing boot for sealing the sharpened insertion end 26b of blunting member cannula 26 may be anchored, as is well-known in the art.

Figure 1D:
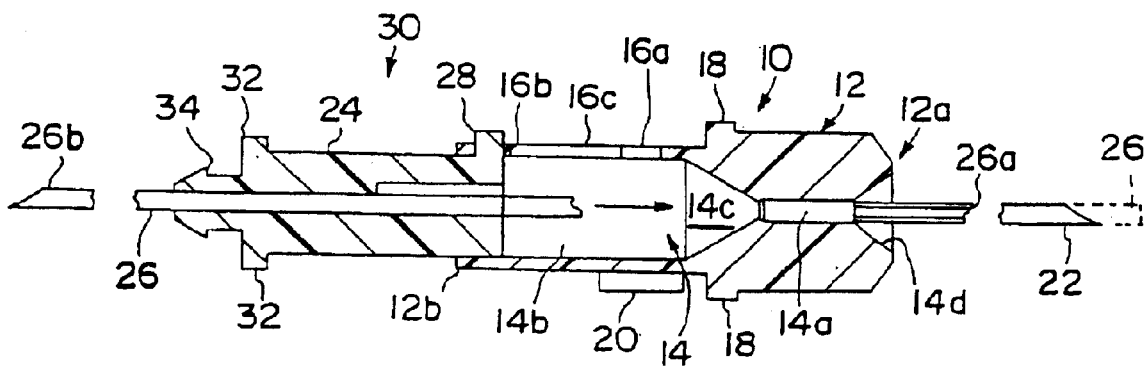
FIG. 1D is a cross-sectional view of a safety needle assembly comprising the hub and shuttle of FIGS. 1A and 1B with a needle cannula and blunting cannula secured therein.

FIG. 1D shows a safety needle assembly 30 that comprises needle hub 10, a hollow needle cannula 22 mounted therein, shuttle 24 and a hollow second cannula 26 mounted therein. Needle cannula 22 has a blunt proximal end that is inserted into the first end 12a of hub 10 and is secured therein by means of adhesive (not shown). The distal end of needle cannula 22 comprises a puncture tip. Passageway 14 defines a proximal insertion region 14d that converges rearward from first end 12a and thus facilitates the insertion of the blunt end of needle cannula 22 into passageway 14. The shuttle portion 14b of passageway 14 is dimensioned and configured to slidably receive shuttle 24 therein. A portion of second cannula 26 extends forward from shuttle 24 through passageway 14 and into needle cannula 22, within which it is telescopically disposed and wherein it terminates at a first, blunt end. The forward extending portion of second cannula 26 is referred to herein as the blunting member 26a. Second cannula 26 and needle cannula 22 cooperate to form a fluid flow passageway that extends through both of them. Thus, the blunting member 26a and the needle cannula 22 are disposed telescopically one within the other without obstructing flow through the needle passageway. Preferably, insertion region 14c converges to a diameter that is smaller than the internal diameter of needle cannula 22 and it is aligned therewith so that it provides a stop for the insertion of needle cannula 22 into body 12 as well as guiding blunting member 26a of blunting member cannula 26 into the proximal end of needle cannula 22. Second cannula 26 also extends rearward from shuttle 24, terminating at a second, sharp end (sometimes referred to herein as a "filling needle") for puncturing the seal on a collection tube and for providing a conduit to establish fluid flow communication between the collection tube and needle cannula 22, as will be described below. Second cannula 26 is securely mounted within shuttle 24 so that it moves with shuttle 24.

Detent 28 on shuttle 24 is dimensioned and configured to protrude through, and to be secured within, locking notches 16b and 16a, to secure the relative positions of shuttle 24 and needle hub 10. FIG. 1D shows needle assembly 30 in an insertion configuration (sometimes referred to herein as the "sharp configuration"), in which shuttle 24 is in a retracted position in hub 10. As shown, assembly 30 is locked in the sharp configuration by the engagement of detent 28 in rear locking notch 16b. Pressing detent 28 into passageway 14 disengages the detent from notch 16b so that shuttle 24 may be advanced within passageway 14. Detent 28 can slide along channel 16c until it engages forward locking notch 16a, thus securing shuttle 24 in an advanced or extended position within needle hub 10, resulting in a blunted configuration in which the blunt end of blunting member 26a protrudes beyond the sharp tip of needle cannula 22 (as indicated in dotted outline), blunting the needle assembly.

Figure 2:
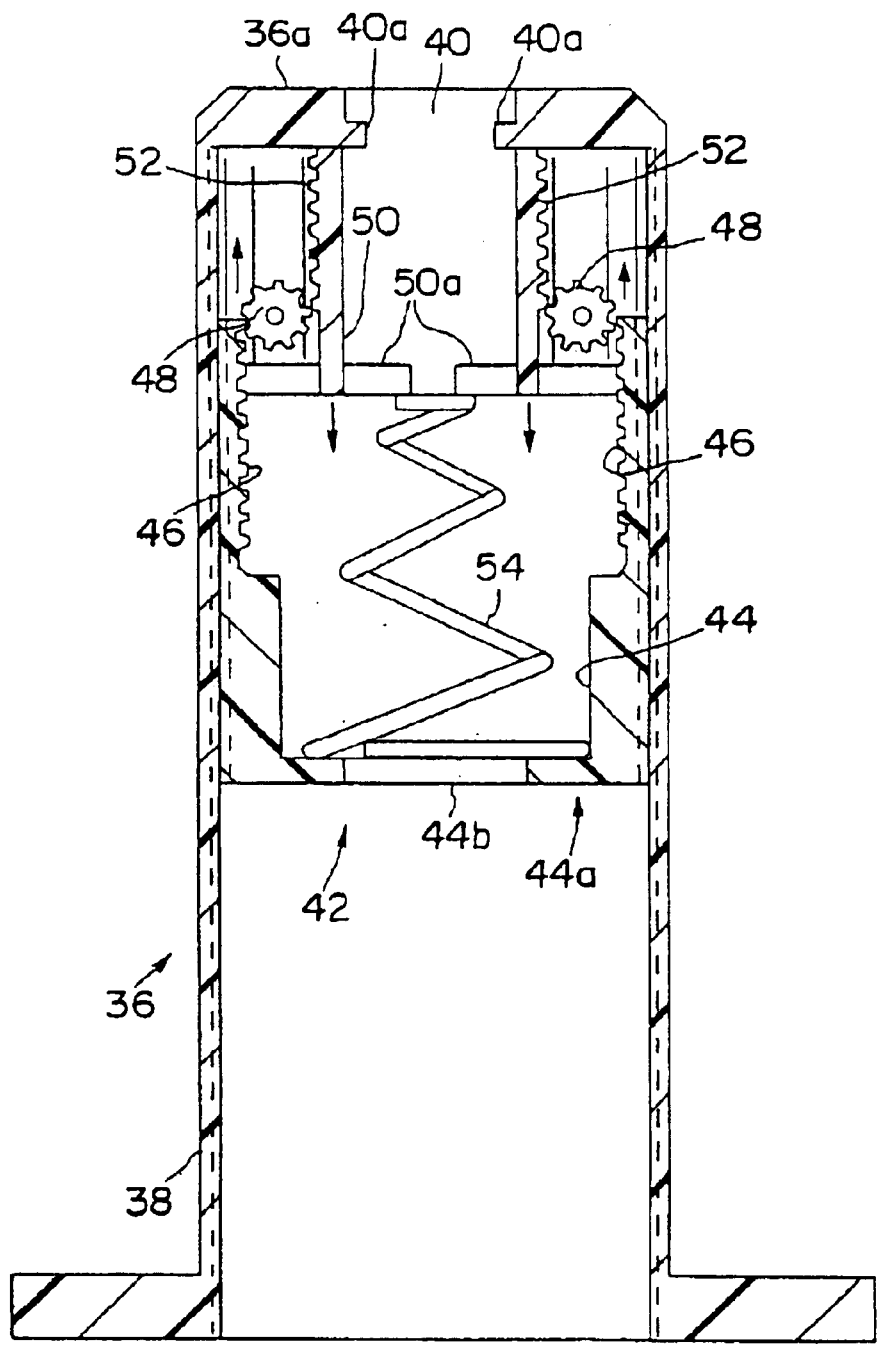
FIG. 2 is a cross-sectional view of a collection tube holder and a blunting mechanism for use with the present invention.

One embodiment of a needle assembly holder in accordance with the present invention is shown in FIG. 2. Holder 36 comprises a cylindrical shell 38 that defines a needle aperture 40 at its forward end. Aperture 40 is dimensioned and configured to receive a needle assembly comprising a needle cannula and a blunting member that are telescopically and movably disposed one within the other, such as needle assembly 30 (FIG. 1D). An annular flange 40a protrudes into aperture 40 and defines notches (not shown) that are sized to allow spline 20 and detent 28 to pass therethrough as needle hub 10 is inserted into aperture 40. Flange 40a, however, is dimensioned and configured to engage hub flange 18 of needle assembly 30 (FIG. 1D). Flange 40a may be configured to be received in a friction fit between flanges 18 and spline 20 (FIG. 1D) when hub 10 is inserted into aperture 40 as far as flanges 18 and 40a will permit and then rotated to move spline 20 out of alignment with the notch in flange 40a. A stop lug (not shown) is positioned in aperture 40 to engage spline 20 upon such rotation and thus limit the rotation to a suitable turn, e.g., 45 degrees. Needle assembly 30 may thus be mounted in holder shell 38.

Shell 38 contains a mechanism 42. Mechanism 42 comprises a transmitting sleeve 44 comprising racks 46 which, in the illustrated embodiment, comprise toothed splines. Mechanism 42 further comprises pinions 48 which, in the illustrated embodiment, comprise toothed gears, and an actuator ferrule 50 comprising racks 52. Mechanism 42 also includes a spring 54. Pinions 48 engage racks 46 and 52 and thus serve as a link between them. In this embodiment and in the others described herein, the link member and its manner of connection to the transmitter, to the shell and to the actuator serve as means for moving the actuator in the holder in an opposite direction from that of the transmitter. Transmitting sleeve 44 is slidably disposed in the interior of shell 38 and racks 46, which are preferably diametrically opposed from one another in shell 38, are slidably disposed in axial grooves in the interior wall of shell 38. Transmitting sleeve 44 has at its coupling end 44a an access aperture 44b. Coupling end 44a is dimensioned and configured to engage the filling end of a conventional collection tube and aperture 44b permits the sharp end of a filling needle such as the end of cannula 26 (FIG. 1D) to protrude therethrough into a collection tube. Pinions 48 are mounted in shell 38 and are dimensioned and configured to rotatably engage racks 46 of transmitting sleeve 44. FIG. 2 shows mechanism 42 in a deployed configuration, i.e., a configuration in which actuator ferrule 50 is positioned forward in shell 38, where it can be retracted or withdrawn (moved downward, as sensed in the FIG.), as will be described herein. (This position is referred to as "deployed". When the actuator ferrule engages a blunting member in this position, the blunting member is extended, to blunt the needle, as will be described herein.) Spring 54, between end cap 50a of actuator ferrule 50 and transmitting sleeve 44, is lightly compressed to bias the mechanism into the illustrated pre-filling position and is situated so that it is tensioned against the transmitting sleeve 44 when transmitting sleeve 44 and actuator ferrule 50 approach each other as described below. Actuator ferrule 50 is disposed within shell 38 and comprises a pair of racks 52 that engage pinions 48. The interior of ferrule 50 is dimensioned and configured to permit the insertion and rotation of needle assembly 30 therein as is necessary to mount needle assembly 30 in shell 38, without depressing detent 28 (FIG. 1D). For example, ferrule 50 may have an L-shaped groove on its interior surface, with detent 28 moving in an axial or longitudinal leg of the groove as needle assembly 30 is inserted into shell 38. Detent 28 may then move in a circumferential leg of the groove when needle assembly 30 is rotated in aperture 40. Alternatively, ferrule 50 may have an internal lug or fillet positioned to engage detent 28 only after needle assembly 30 is mounted in shell 38 and ferrule 50 is moved rearward.

Analogously to the interrelation on needle assembly 30 (FIG. 1D) of spline 20 and annular flange 40a, the shuttle flanges 32 on shuttle 24 are eccentrically configured about the longitudinal axis of the device, and actuator ferrule 50 forms a cap aperture in cap 50a that is configured to align with flanges 32 and permit them to pass therethrough upon initial insertion of needle assembly 30 into shell 38. Spring 54 is configured so that, when the shuttle flanges 32 pass through the aperture in cap 50a, they engage spring 54. The rotation of needle assembly 30 that mounts the assembly in shell 38 also turns flanges 32 out of alignment with the aperture so that cap 50a can thereafter engage the flanges 32 under the force of spring 54. Actuator ferrule 50 can thus engage blunting member 26a, via shuttle 24.

Mechanism 42 is dimensioned and configured so when transmitting sleeve 44 is moved forward within shell 38 (e.g., as a result of the insertion of a collection tube), actuator ferrule 50 moves in the reverse direction, away from forward end 36a, under the operation of pinions 48. Mechanism 42 thus moves from the pre-filling configuration shown in FIG. 3 to a filling configuration. Such movement also imposes further tension or compressive force on spring 54.

Figure 3:
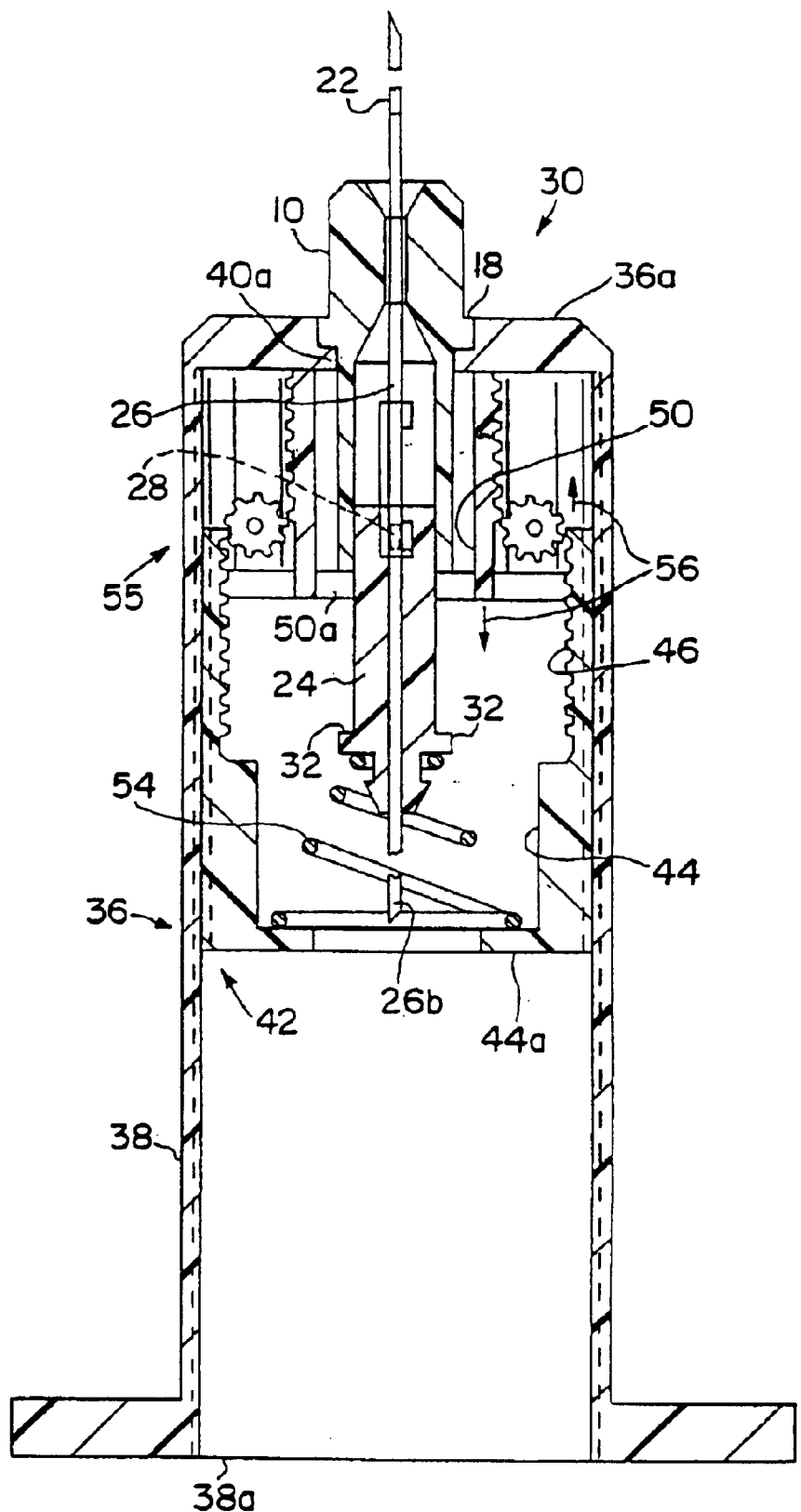
FIG. 3 is a cross-sectional view of a passive blood collection needle in accordance with a particular embodiment of the present invention, comprising the holder and blunting mechanism of FIG. 2 and the needle assembly of FIG. 1D.

The fully assembled blood collection needle 55 is shown in FIG. 3 with needle assembly mounted in aperture 40 (FIG. 2). The needle cannula 22 is in fixed relation to the holder because of the engagement of annular flange 40a (FIG. 2) with flange 18 (FIG. 1D) and spline 20 (FIG. 1D, not seen in FIG. 3). Collection needle 55 is in an initial, pre-filling configuration in which needle assembly 30 is in a sharpened configuration even though actuator ferrule 50 is in a deployed position, because shuttle 24 on blunting member 26a has not yet engaged actuator ferrule 50. Note that shuttle flanges 32 of needle assembly 30 protrude beyond end cap 50a (FIG. 2) of ferrule 50 and compress spring 54. Shuttle 24 resists being moved by spring 54 forward into hub 10 because detent 28 is locked in notch 16b (FIG. 1A), leaving needle assembly 30 locked in the sharp configuration, ready for venipuncture.

Figure 4B:
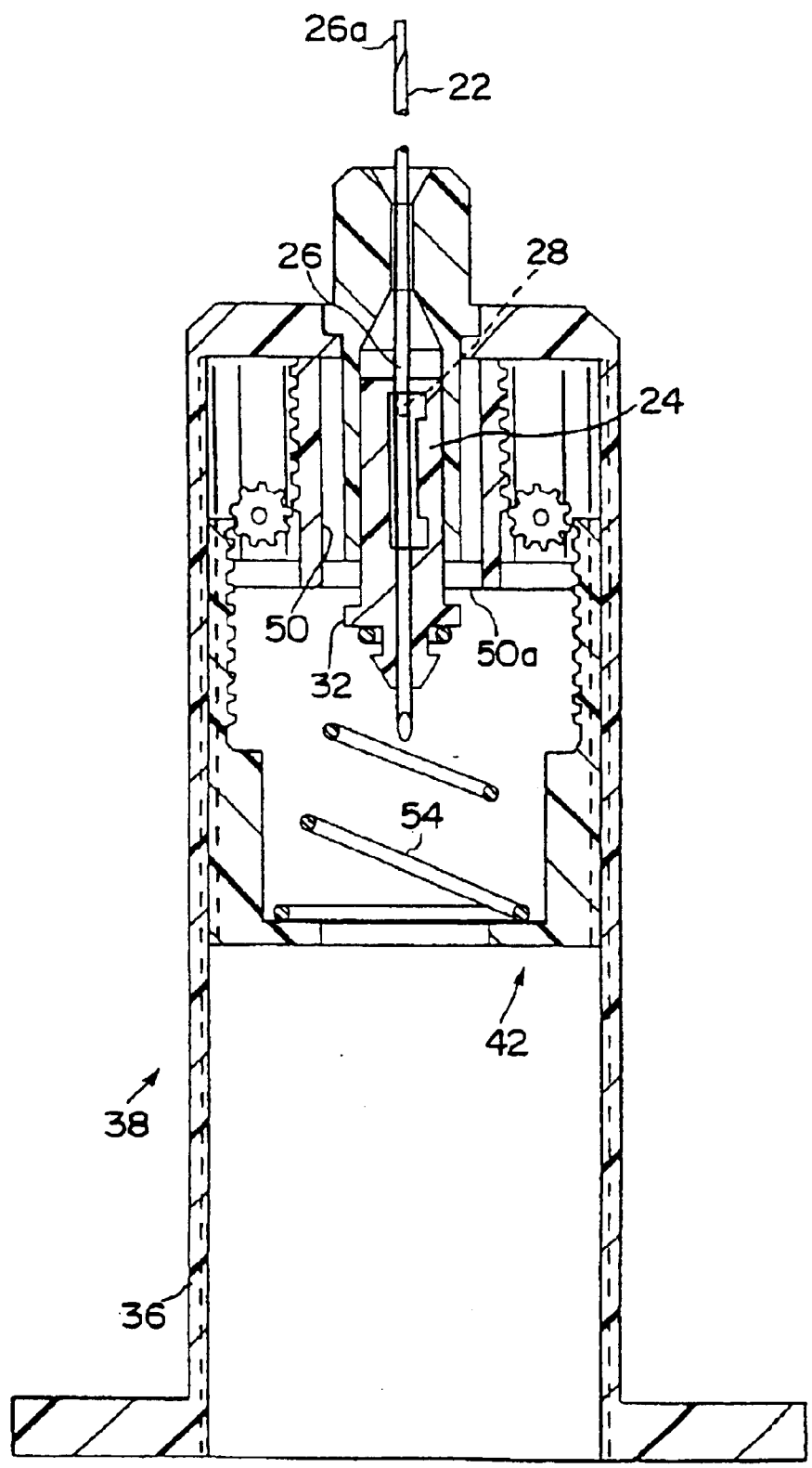

To prepare blood collection needle 55 for use, a technician will typically install needle assembly 30 in holder 36 as shown in FIG. 3, and then remove from needle cannula 22 a protective sheath (not shown) and insert needle cannula 22 into a patient's vein. Then, the technician will take a conventional collection tube 56a (FIG. 4A) and insert the capped end thereof into the open end 38a of shell 38 with sufficient force to assure that filling needle 26b punctures the seal cap 56b on the collection tube, thus establishing flow communication between the collection tube and the needle assembly. This action will impose sufficient force on coupling end 44a to drive transmitting sleeve 44 forward in needle holder 36 (upward as sensed in FIG. 3) and will compress spring 54. The operation of mechanism 42 will transfer the forward motion of transmitting sleeve 44 into rearward movement of actuator ferrule 50 indicated by arrows 56 (downward, as sensed in FIG. 3), under the operation of pinions 48. Thus, mechanism 42 causes actuator ferrule 50 to move in a direction opposite from that of transmitting sleeve 44. The interior of ferrule 50 is configured so that such rearward movement causes it to depress detent 28 and thus unlock the needle assembly. Shuttle flanges 32 then bear on end cap 50a under the force of spring 54. This motion will conclude with mechanism 42 in the retracted configuration shown in FIG. 4A, in which actuator ferrule 50 and shuttle 24 are in their retracted positions due to the advancement of transmitting sleeve 44, leaving needle assembly 30 in the sharpened configuration. With the forward end of needle cannula 22 in a patient's vein and the filling needle 26b of second cannula 26 in an evacuated collection tube, blood will flow through the fluid flow passageway of the device to fill the collection tube. It is advantageous for the needle assembly 30 to be sharp while the sample tube is filling because the filling process may be interrupted if the needle is jostled or obstructed and it may be necessary for the technician to re-position the needle in the vein; this is better accomplished with a sharp needle than a blunt one. Upon subsequent withdrawal of the collection tube 56a from shell 38, transmitting sleeve 44 will move according to the bias of spring 54 in the direction of arrows 58. The operation of the mechanism 42 will, accordingly, move actuator ferrule 50 in the opposite direction, towards its forward (upward), pre-filling position. Shuttle 24 will also move forward (upward, as sensed in the Figure) with ferrule 50, under the impetus of spring 54, so that the blunt end of the blunting member 26a is extended beyond the tip of needle cannula 22, thus blunting the device. Shuttle 24 locks in the forward position with the blunting member 26a extending beyond the puncture tip of needle cannula 22 before actuator ferrule 50 stops its forward movement. The additional forward movement of actuator ferrule 50 relative to shuttle 24 allows the internal fillet or groove that previously unlocked the needle assembly to disengage from the locking detent. Accordingly, detent 28 can engage locking notch 16a to lock needle assembly 30 in the blunted configuration. The additional forward movement of ferrule 50 also causes end cap 50a to disengage from shuttle flanges 32. Mechanism 42 comes to rest in the deployed configuration shown in FIG. 4B. Subsequent insertion of another collection tube will cause the actuator ferrule 50 to move rearward again, unlocking shuttle 24 and then engaging shuttle flanges 32 to return to the sharpened configuration shown in FIG. 4A, and removal of the tube thereafter will once again return the device to the blunted configuration of FIG. 4B. Thus, after the initial insertion of a sample tube, mechanism 42 serves to move actuator ferrule 50 and the blunting member 26a in a direction contrary to that of the sample tube and transmitting sleeve 44 in the holder shell. Such motion is illustrated as changes between the configurations of FIGS. 4A and 4B.

In an alternative embodiment, actuator ferrule 50 may carry locking flanges disposed about the central aperture of end cap 50a (FIG. 2). Such locking flanges may be configured to engage shuttle flanges 32 (FIG. 1D) when the first insertion of a blood collection tube moves actuator ferrule 50 rearward from the initial configuration (FIG. 3) to the filling configuration shown in FIG. 4A.

In an alternative aspect of this invention, a mechanism in accordance with the present invention may incorporate a cam and follower arrangement instead of a rack and pinion arrangement. In such an embodiment, a rotating cylindrical cam (referred to herein as a "rotator") will be disposed within the cylindrical body of the needle holder carrying the self-blunting needle assembly. An actuator structure (or "inner sleeve") that engages the blunting member will follow the cam surface of the rotator. When the rotator rotates within the needle holder, the actuator follows by imposing a corresponding axial motion on the blunting member in accordance with the direction of rotation of the rotator. The device is configured so that the forward insertion of a sample tube into the needle holder rotates the rotator in a direction that causes the actuator to retract (rearward) within the needle holder. The rotating cam embodiment of the present invention, like the rack and pinion embodiment, creates contrary motion between the blunting member and the sample tube inserted into the holder with each insertion and withdrawal of a tube, except for the first time a collection tube is inserted into the holder. Such a device can employ the safety needle assembly 30 of FIG. 1B, as described below.

Figure 5A:
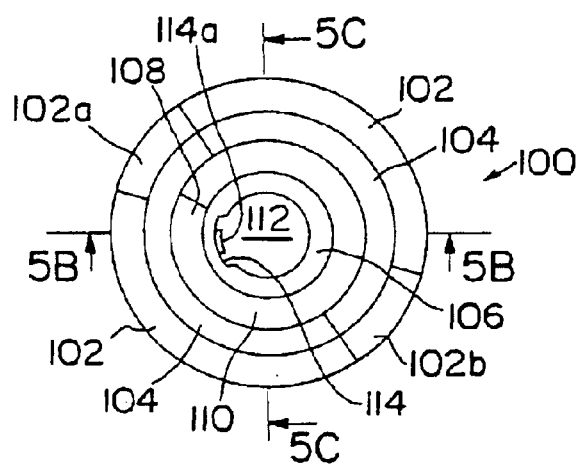
FIG. 5A is a schematic plan view of a rotator element for use in a blunting mechanism in accordance with another embodiment of the present invention.
Figure 5B:
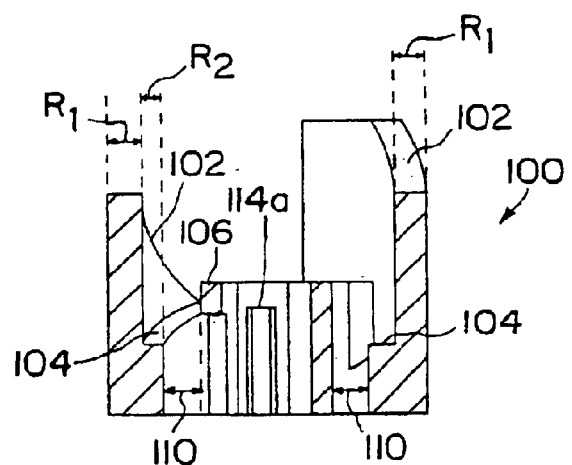
FIG. 5B is a cross-sectional view of the element of FIG. 5A taken along line 5B—5B.
Figure 5C:
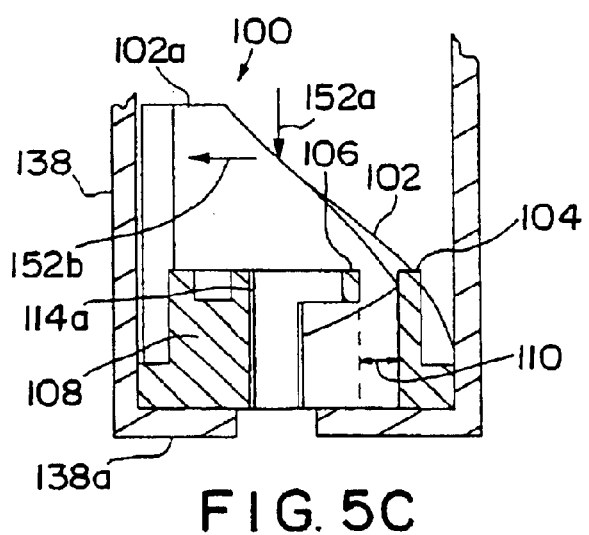
FIG. 5C is a cross-sectional view of the element of FIG. 5A taken along line 5C—5C.

FIGS. 5A, 5B and 5C provide related views of a cylindrical cam or "rotator" 100 for use in one embodiment of the present invention. In the plan view of FIG. 5A, rotator 100 is seen to have a round periphery, thus allowing for coaxial rotation within a cylindrical needle holder. Rotator 100 has three principal concentric annular segments: at least one following surface 102, at least one driving surface 104 and a central collet 106. Following surfaces 102 are disposed in the circumferential, outermost annular segment of rotator 100, which includes a flat upper surface 102a and a flat lower surface 102b. Driving surfaces 104 are concentrically contiguous with following surfaces 102. Proceeding radially inward, the next annular segment of rotator 100 is collet 106, which is physically connected to surfaces 102 and 104 by a bridge 108. Bridge 108 spans a region between collet 106 and driving surfaces 104 that is occupied principally by a curvate gap 110. The interior region 112 of collet 106 defines a recess 114 within which is disposed an unlocking fillet 114a. Fillet 114a is better viewed in FIG. 5B, which also shows that the following surfaces 102 occupy a first annular region R1 and driving surfaces 104 occupy the contiguous annular region R2.

As is evident from FIG. 5C, rotator 100 can be disposed within the generally cylindrical shell 138 of a needle holder, rotatably resting on the bottom shoulder 138a of shell 138. So disposed, the impingement of an axial force as indicated, e.g., by arrow 152a, on following surface 102 will cause rotator 100 to rotate in the direction of arrow 152b. If the structure imposing the force at arrow 152a is not permitted rotational movement as it bears on surface 102, it will move downward (axially) as rotator 100 rotates. Since driving surfaces 104 slope in a helical direction opposite from that of following surfaces 102, a structure that is slidably disposed on surface 104 and that is constrained against rotation will move upward on the contrary incline of driving surface 104 as the structure on surface 102 moves downward, as will be discussed further below.

Figure 6:
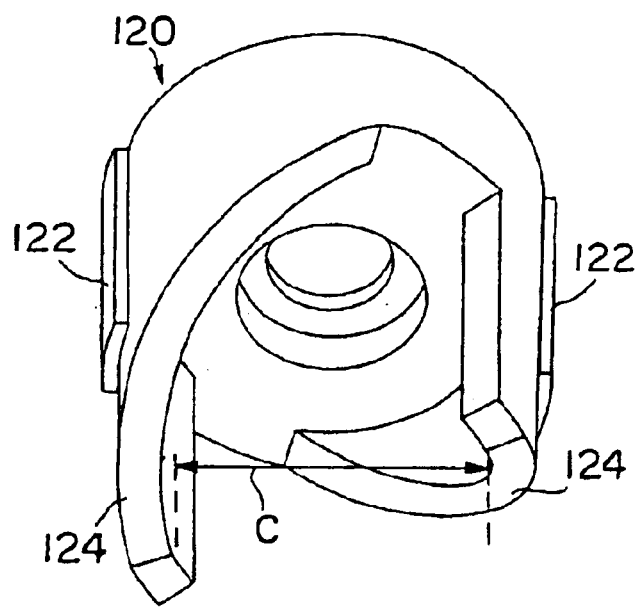
FIG. 6 is an exploded perspective view of a transmitter element and an actuator element for use with the rotator element of FIG. 5A in a blunting mechanism in accordance with the present invention.
Figure 6:
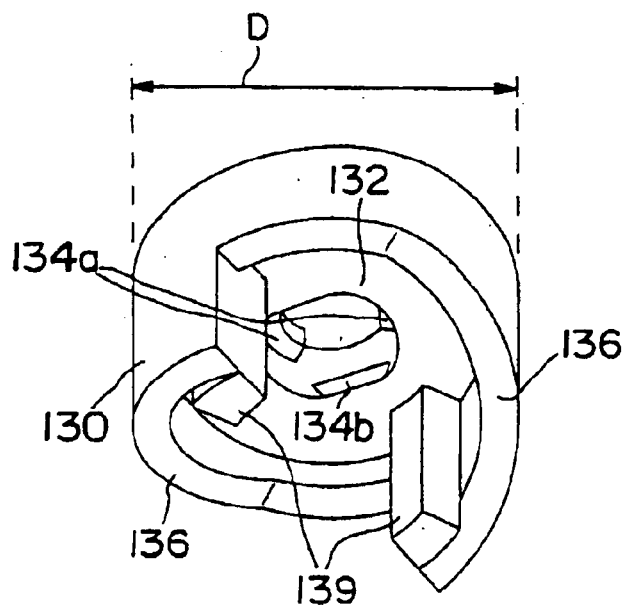

A force transmitter and cam follower/actuator that bear on surfaces 102 and 104, for driving and following rotator 100, are shown in an exploded coaxial relationship in FIG. 6. Transmitter 120 has a generally cylindrical configuration dimensioned to have the same outer diameter as rotator 100 so that the two can fit snugly in the same cylindrical needle holder shell. However, transmitter 120 also comprises guiding means for engaging the interior surface of the shell so that transmitter 120 will be inhibited against free rotational motion within the shell. Preferably, it will be constrained for axial motion within the shell. In the embodiment of FIG. 6, the guiding means of transmitter 120 comprises a pair of peripheral guiding fillets 122 that are dimensioned and configured to be slidably received within axially-extending grooves in the interior wall of the shell within which transmitter 120 is disposed. With the fillets 122 disposed in such grooves, transmitter 120 will be able to move axially, i.e., longitudinally, within the holder shell, but will not be able to rotate therein. Transmitter 120 comprises a pair of driving surfaces 124 that are dimensioned and configured to engage following surfaces 102 of rotator 100 in annular region R1, within which they define a cylindrical receiving region C.

Also shown in FIG. 6 is actuator 130 which has a cylindrical outer configuration having a diameter D dimensioned to be received within receiving region C of transmitter 120. Actuator 130 has a central aperture 132 into which locking tabs 134a, 134b extend, for engaging the shuttle flanges 32 of needle assembly 30 (FIG. 1B). Actuator 130 defines a pair of following surfaces 136 that are dimensioned and configured for complementary engagement with driving surfaces 104 in annular region R2 of rotator 100. However, actuator 130 is constrained against rotational movement by the engagement of internal lugs 139 with a pair of posts (not shown) that extend upward from bottom shoulder 138a of shell 138 and which protrude through rotator 100 via gap 110.

Figure 7A:
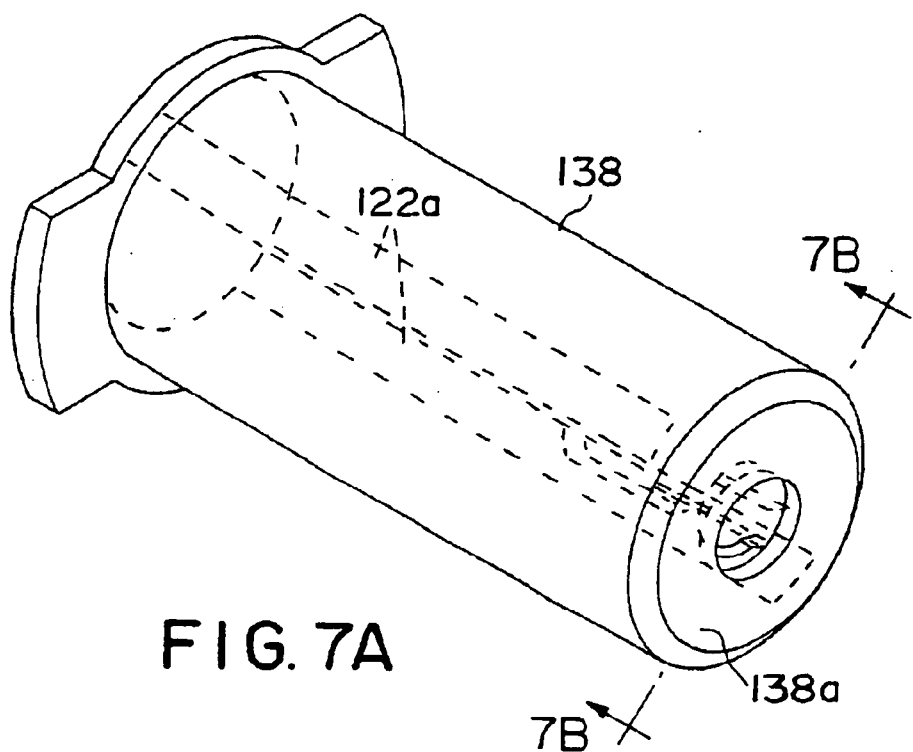
FIG. 7A is a perspective view of a sample tube holder for use with the elements shown in FIGS. 5A and 6.
Figure 7B:
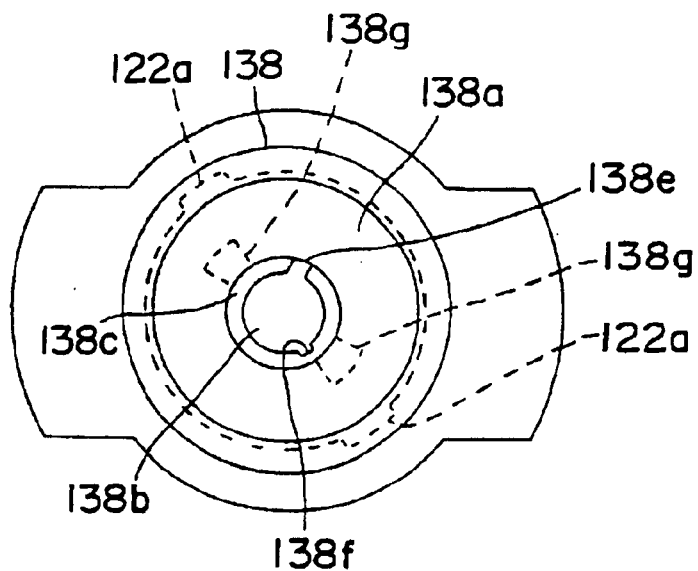
FIG. 7B is a view of the holder of FIG. 7A taken along line 7B—7B.

FIG. 7A provides a perspective view of a sample tube holder that may house a mechanism comprising the rotator 100, transmitter 120 and actuator 130 of FIGS. 5A, 5B, 5C and FIG. 6. The holder comprises a shell 138 having a longitudinal axis A and a shoulder 138a at its forward end. Shell 138 defines a pair of internally, axially disposed grooves 122a, shown in dotted outline. FIG. 7B provides an end view of shell 138, showing aperture 138b which is dimensioned and configured to receive safety needle assembly 30 of FIG. 1D. Aperture 138b is substantially circumscribed by a flange 138c that is dimensioned and configured to permit the blunting component and rearward portion of the needle hub therein, but to engage hub flanges 18 (FIG. 1D), leaving the first end 12a of needle hub 12 extending forward from shoulder 138a. Notch 138e is configured to receive a locking spline 20 (FIG. 1D), and notch 138f is dimensioned and configured to allow the detent 28 (FIGS. 1C and 1D) to pass through aperture 138b to avoid unlocking the needle assembly as it is first being inserted into shell 138. After insertion of the needle assembly into the aperture, the needle assembly is rotated so that the locking spline and flanges 18 engage flange 138c. Also seen in FIG. 7B are two posts 138g that extend axially from shoulder 138a towards the rearward end of shell 138.

Figure 8B:
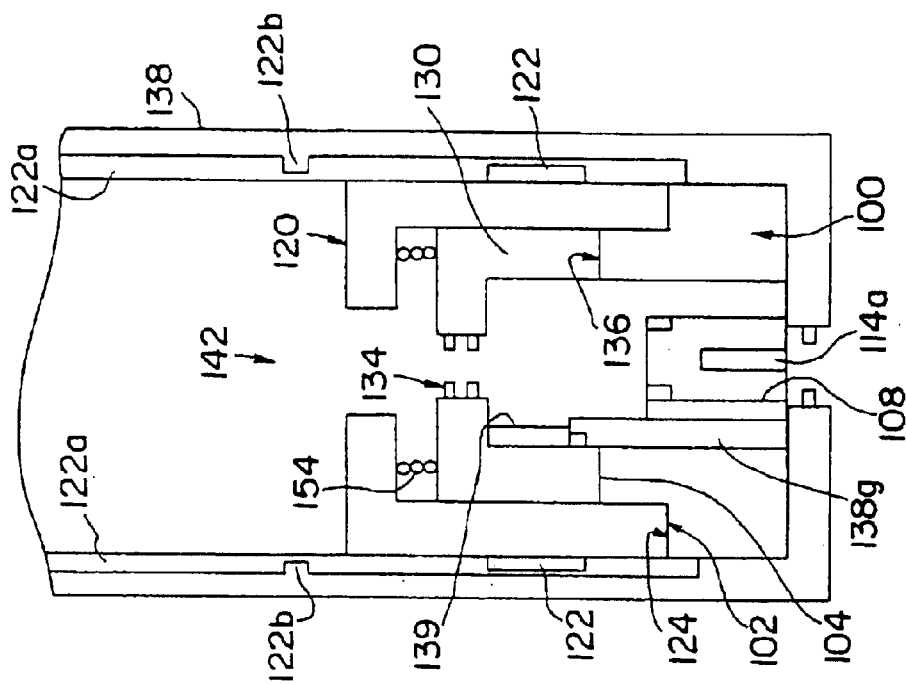
FIGS. 8A and 8B are schematic cross-sectional views of a passive blood collection needle comprising the elements shown in FIGS. 5A, 6 and 7A, in the blunted and insertion configurations, respectively, with the needle assembly omitted to clarify the drawing.
Figure 8A:
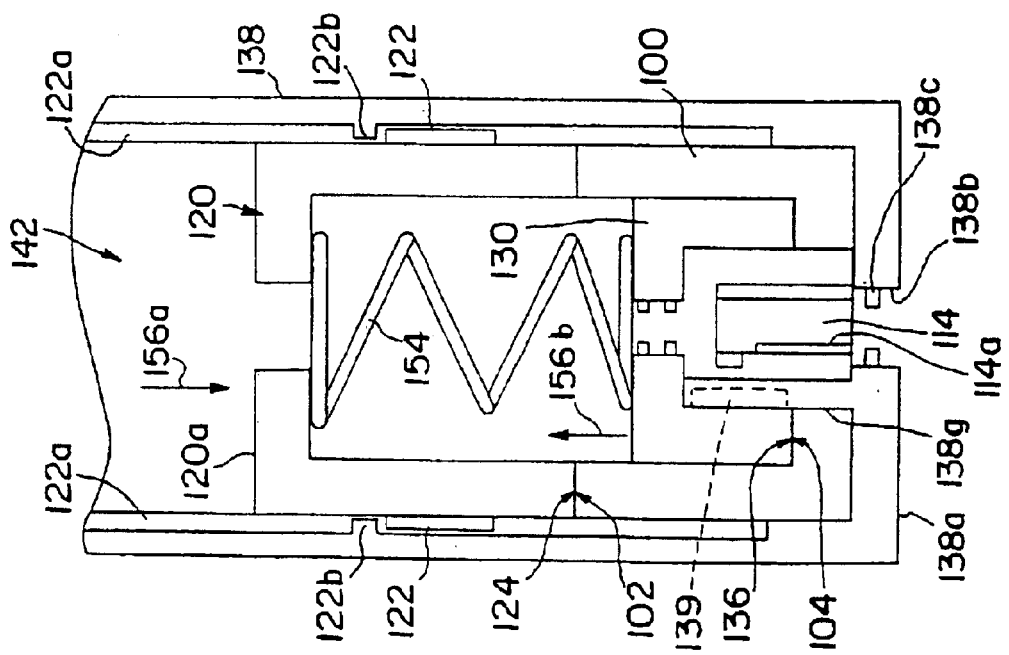

FIGS. 8A and 8B are cross-sectional schematic drawings that indicate the relative positions of the transmitter 120, rotator 100 and actuator 130 in two different configurations within shell 138. FIG. 8A depicts the holder mechanism in the deployed configuration. In this configuration, rotator 100 is rotatably situated within shell 138 and, because it is resting on shoulder 138a, it is constrained against forward axial movement. The transmitter 120 is disposed in shell 138 so that the lower (as sensed in FIG. 8A) portions of its helical driving surfaces 124 engage the upper portions of the following surfaces 102 of rotator 100. Transmitter 120 carries fillets 122 that engage grooves 122a in shell 138 and thus permit axial sliding motion of transmitter 120 in shell 138 but prevent rotational motion. Actuator 130 is disposed within the outermost annular region of rotator 100, with following surfaces 136 engaging driving surfaces 104. An internal post 138g extending from shell 138 through gap 110 (FIG. 5B) engages lug 139 to prevent actuator 130 from rotating within shell 138. A spring 154 is disposed axially between transmitter 120 and actuator 130.

When a forward (downward, as sensed in the Figure) force is imposed on bearing surface 120a of transmitter 120, e.g., by pressing a sample collection tube into shell 138, transmitter 120 moves downward, as indicated by arrow 156a and the spiraled driving surface 124 bears upon the complementary following surface 102 of rotator 100. Since transmitter 120 is constrained against rotation, transmitter 120 acts as a driving cam follower and the downward motion of transmitter 120 causes rotator 100 to rotate within shell 138. Such rotation of rotator 100 will cause driving surface 104 to impose a force upon following surface 136 of actuator 130. Since actuator 130 is constrained against rotational motion by the engagement of lugs 139 with the posts 138g extending upward from shoulder 138a, the force imposed by driving surface 104 will cause actuator 130 to move upwards (as indicated by arrow 156b). Thus, rotator 100 serves as a linking member that moves actuator 130 in a direction opposite from that of transmitter 120. The result of the downward axial motion of transmitter 120 is the retracted configuration depicted in FIG. 8B, which shows rotator 100 in a rotated position and actuator 130 in an elevated position relative to FIG. 8A.

As transmitter 120 and actuator 130 move towards each other from the pre-filling configuration of FIG. 8A to the filling configuration of FIG. 8B, they compress spring 154. The friction fit of a collection tube in shell 138 is sufficient to withstand the tendency of spring 154 to decompress and move transmitter 120 (and the collection tube pressing against it) upward. However, upon manual removal of the collection tube, spring 154 will drive transmitter 120 upward so that it remains in contact with the collection tube until it encounters a stop lug on the interior wall of shell 138, e.g., lug 122b in groove 122a. During the withdrawal process, the upward motion of transmitter 120 will tend to disengage driving surface 124 from following surface 120. However, the residual downward force imposed by spring 154 on actuator 130 will cause following surface 136 to bear on driving surface 104, to which rotator 100 will respond by rotating sleeve 138 until following surface 102 again engages driving surface 124. Further withdrawal of the collection tube will allow spring 154 to drive transmitter 120 still higher and actuator 130 still lower in shell 138, thus imposing further rotation on rotator 100 until the configuration of FIG. 8A is regained.

Figure 8C:
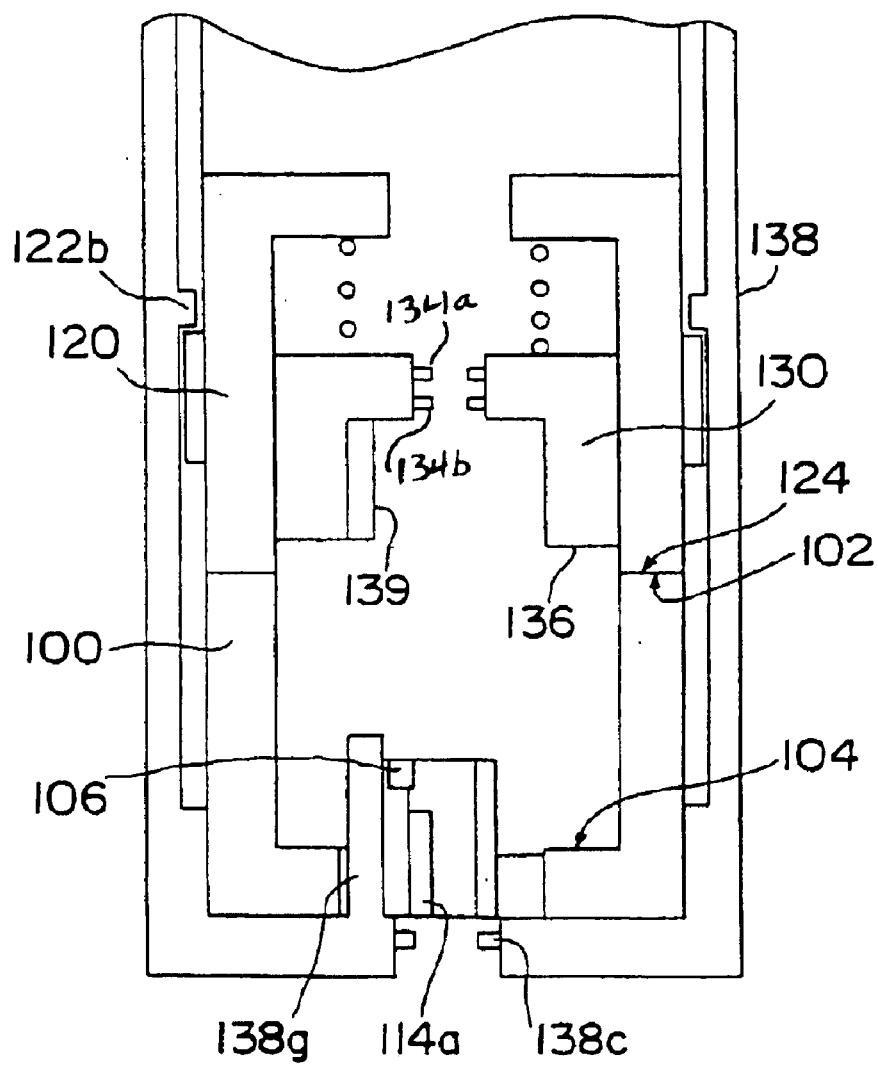
FIG. 8C is a view similar to FIGS. 8A and 8B of the blunting mechanism as it will be configured upon the initial installation of a locked needle assembly prior to insertion of a sample collection tube.

As with the rack and pinion embodiment of FIGS. 1 through 4B, the needle assembly is first inserted into the shell 138 in the sharpened configuration (shown in FIG. 1D) with mechanism 142 in the deployed configuration of FIG. 8A. As needle assembly 30 is inserted into aperture 138b, detent 28 (FIG. 1D) passes through notch 138f (FIG. 7B) of shell 138, and then alongside fillet 114a (FIG. 5B). Locking spline 20 (FIG. 1D) passes through notch 138e (FIG. 7B), and hub flanges 18 (FIG. 1D) come to a stop against flange 138c (FIGS. 7B, 8A). The needle assembly is rotated to engage flange 138c between spline 20 and flanges 18, thus locking the needle in the holder. This rotation disposes detent 28 beside fillet 114a. Meanwhile, the shuttle flanges 32 bear against locking tabs 134a of actuator 130, pushing actuator 130 upward (as sensed in FIG. 8A) and lifting it off rotator 100 to the position shown in FIG. 8C. The rotation of needle assembly 30 that engages flange 138c also positions shuttle flanges 32 (FIG. 1B, 1D) between locking tabs 134a and 134b. Transmitter 120 and rotator 100 are in a deployed configuration, but actuator 130 is retracted and the needle assembly is sharp.

When the first sample tube is inserted into holder shell 138, it bears on transmitter 120, which moves downward, causing rotator 100 to rotate. This makes fillet 114a swipe surface 28a (FIG. 1C) on detent 28 and unlock the needle assembly. Shuttle 24 then allows actuator 130 to move forward (downward as sensed in FIG. 8A), but only until its following surface 136 engages driving surface 104 of rotator 100. The apparatus is configured so that this occurs before the blunting member blunts the needle. The continued rotation of rotator 100 in response to the further insertion of the sample tube then moves actuator 130 back upwards. At the point of full insertion of the sample tube, the device reaches the retracted configuration of FIG. 8B, in which tabs 134b of actuator 130 hold shuttle 24 (not shown) in the retracted position, leaving the needle assembly in the sharpened configuration. Upon withdrawal of the sample tube, spring 154 drives the device back to the deployed configuration of FIG. 8A, and actuator 130 advances shuttle 24 forward, blunting the needle. Insertion of yet another collection tube will bring the device back to the sharpened configuration of FIG. 8B.

Figure 8D:
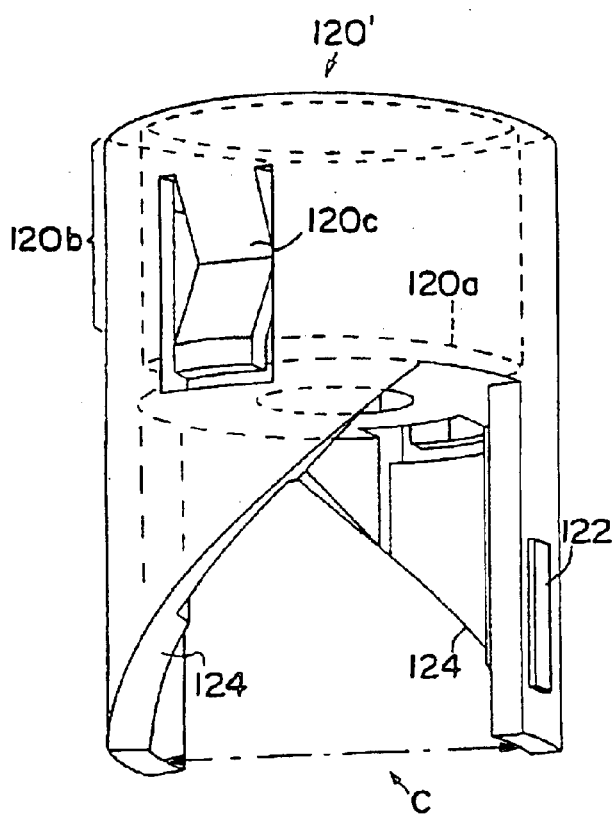
FIG. 8D is an elevation view of a transmitter device of a blunting mechanism according to yet another embodiment of this invention.
Figure 8E:
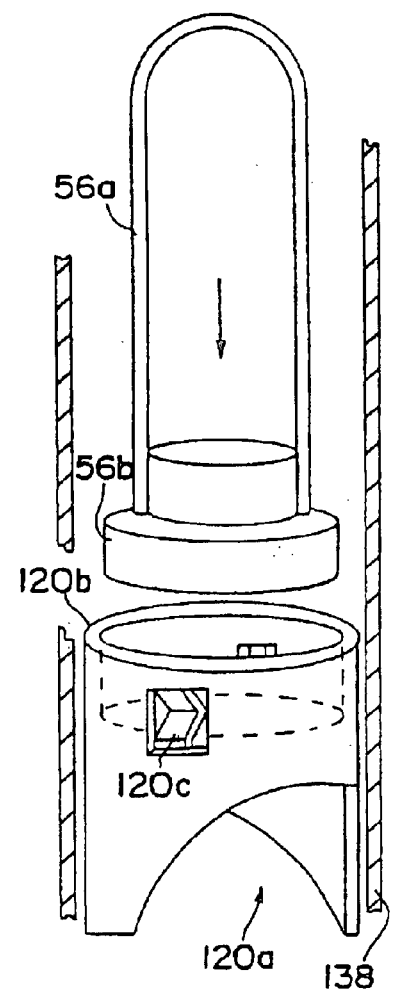
FIG. 8E is an elevation view of the transmitter device of FIG. 8D together with a blood collection tube in a holder shell shown in cross section.

In accordance with another embodiment of the invention, the transmitter may be dimensioned and configured to engage the sample collection tube. For example, a transmitter 120'0 shown in FIG. 8D has a generally cylindrical configuration that defines a cylindrical receiving region C and driving surfaces 124 corresponding to those of transmitter 120 (FIG. 6). In addition, however, transmitter 120' comprises a receiving ferrule 120b that extends axially from bearing surface 120a in a direction opposite from driving surfaces 124. Receiving ferrule 120b defines an interior region that is dimensioned and configured to receive the seal cap on a conventional sample blood collection tube. In addition, receiving ferrule 120b carries a leaf spring 120c which may optionally be formed integrally therewith as shown in the Figure. Leaf spring 120c protrudes into the interior region of receiving ferrule 120b and it is configured so that it will be displaced by a sample collection tube inserted therein. As suggested in FIG. 8E, a collection tube such as blood collection tube 56a, which carries a seal cap 56b, may be inserted into the cylindrical shell 138 and thus into the receiving ferrule 120b of transmitter 120' therein. As this occurs, seal cap 56b will displace leaf spring 120c outwardly. Leaf spring 120c is configured so that such displacement causes it to bear against the interior of the holder shell, thus increasing the friction between transmitter 120' and the surrounding shell 138. This added friction helps keep tube 56a in place during the filling process despite the bias of spring 154.

Figure 9A:
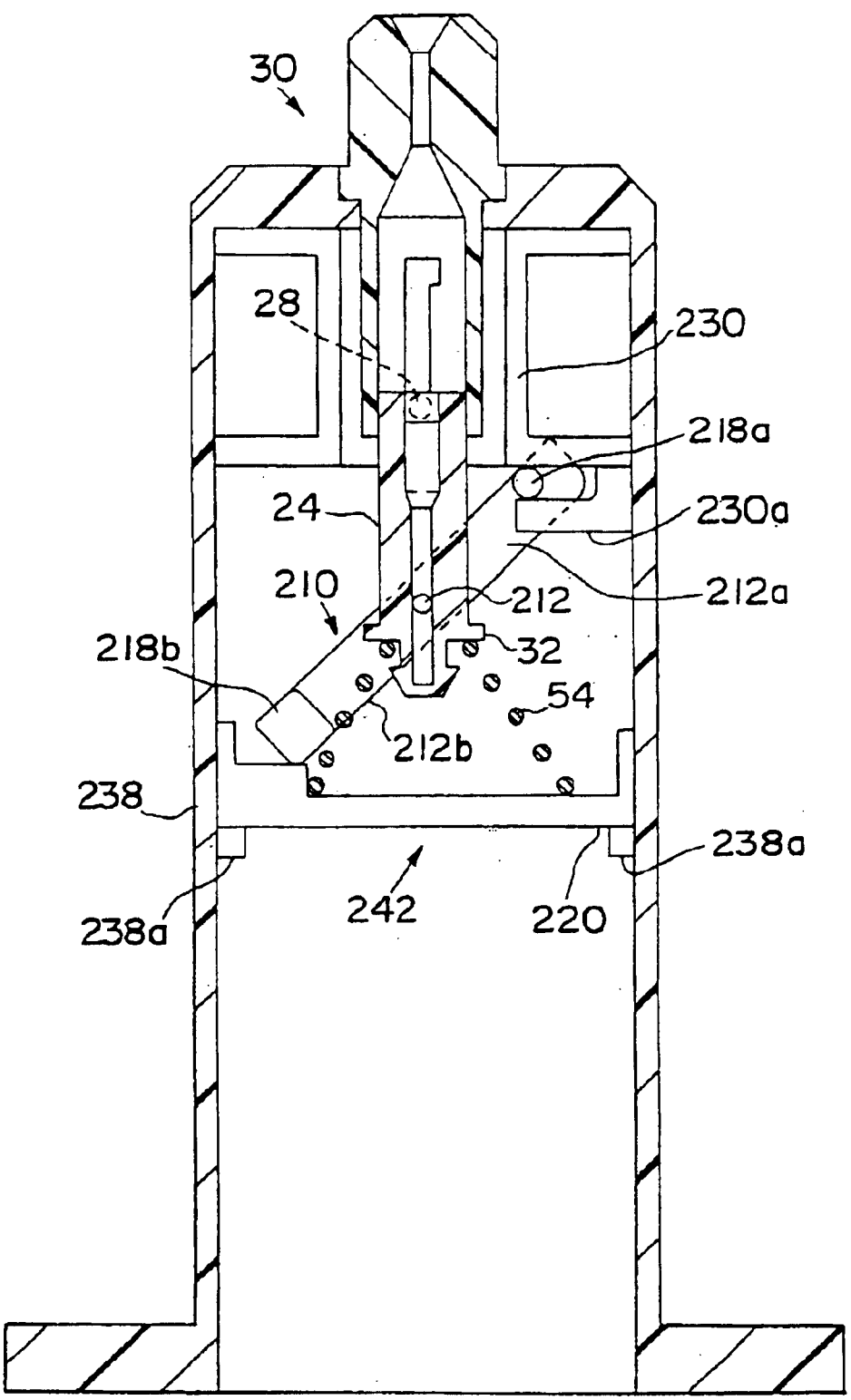
FIG. 9A is a cross-sectional schematic view of a blunting mechanism in a needle holder in accordance with a first lever embodiment of the present invention.

The embodiment of FIG. 9A provides a schematic illustration of a lever-based mechanism for the present invention. Mechanism 242 makes use of a ring lever 210, shown in plan view in FIG. 9B and in perspective view in FIG. 9C. Ring lever 210 is configured in the shape of a ring having a pair of fulcrum studs 212 extending outwardly and coaxially therefrom. Studs 212 define the fulcrum of lever ring 210 and divide ring 210 into two roughly semicircular arms 212a and 212b that extend therefrom. As sensed in FIG. 9A, arm 212a extends upward (or forward) and comprises a pintle 218a for connecting to the actuator 230 in a hingelike manner that permits pintle 218a to move radially so that ring lever 210 can pivot. Arm 212b extends downward (rearward) and comprises a bearing portion 218b for engaging the transmitter baffle 220 in a manner that allows movement corresponding to that of pintle 218a on actuator frame 230. The central region 216 (FIG. 9B) of ring 210 is configured to allow the blunting member and associated shuttle to pass therethrough.

When ring lever 210 is mounted by studs 212 for rotation about their axis, a force applied to a non-axial point on ring 210, as indicated by the application of force F1 at a point diametrically opposite from pintle 218a, will produce a rotation about studs 212. As sensed in FIG. 9C, an upward motion of bearing portion 218b resulting from an upwardly-directed force F1 will produce a contrary, downward motion of pintle 218a, as indicated by arrow F2. Lever ring 210 thus operates as a lever of the first class (one in which the fulcrum is between the applied force and the load).

In accordance with this aspect of the invention, ring lever 210 is mounted inside holder shell 238 with studs 212 rotatably disposed at right angles to the longitudinal axis of the shell. Pintle 218a is connected to an actuator frame 230 by engaging a lift arm 230a connected thereto. A transmitter baffle 220 is mounted within shell 238 for axial sliding motion between a stop member 238a on shell 238 and frame 230. Transmitter baffle 220 defines a large internal aperture (not shown) to permit the filling needle at the rearward end of the blunting member and the blunting member shuttle 24 to pass therethrough. A spring 54 is partially compressed between shuttle flanges 32 and baffle 220.

Actuator frame 230 is slidably disposed within shell 238. It will be apparent that the insertion of a sample collection tube that is pressed against transmitter baffle 220 will apply a force on bearing portion 218b of ring lever 210 at an end thereof opposite from pintle 218a, corresponding to force F1 (FIG. 9C). Ring lever 210 will rotate about studs 212 causing pintle 218a to move in the contrary direction indicated by arrow F2 (FIG. 9C). Since pintle 218a engages the slidable actuator frame 230, the upward (as sensed in FIG. 9A) movement of baffle 220 produces a contrary, downward motion of frame 230.

Actuator frame 230 is configured similarly to actuator ferrule 50 of mechanism 42 (FIG. 3) insofar as it permits the initial installation of needle assembly 30 in shell 238 in the sharp configuration while the mechanism remains in the pre-filling configuration of FIG. 9A. However, the internal configuration of actuator frame 230 will cause it to release detent 28 when it moves rearward (downward as sensed in FIG. 9A) in response to the first insertion of a sample tube into shell 238. Then, the needle is sharp while the device is in the filling configuration. Upon the subsequent removal of the sample collection tube, spring 54 will push shuttle 24 (and the actuator frame 230 bearing thereon) upward, thus moving the mechanism to the deployed configuration and the needle assembly (not fully shown) to the blunted configuration. The subsequent insertion of another sample tube will move baffle 220 upward and the resulting action of ring lever 210 will pull actuator frame 230 and shuttle 24 resting thereon downward in a direction contrary to the direction of insertion of the sample collection tube, moving the mechanism to the retracted configuration and the needle assembly to the sharpened configuration.

In a related lever-type embodiment shown in FIG. 9D, mechanism 242' comprises a transmitter baffle 220', a ring lever 210' and an actuator 230' that are integrally interconnected by hinge straps 218a' and 218b' that are secured thereto. As shown in FIG. 9D, mechanism 242 may be considered a single piece. Hinge straps 218a', 218b' are sufficiently pliable to allow the necessary movement between lever 210' and draw transmitter baffle 220' and actuator 230' as lever 210' pivots to draw baffle 220' and actuator 230' towards each other and then push them apart. Strap hinges 218a' and 218b' may be formed, for example, from a polymeric material. Optionally, transmitter baffle 220' and/or actuator 230' may be formed from the same material as the hinge strap connected thereto and they may be molded together with the hinge strap in a single operation, leaving a distal end of the hinge strap free to be secured to another structure of mechanism 242'. For example, lever 210' may be formed with hinge straps 218a' and 218b' extending therefrom, and the distal ends of the straps may be secured to baffle 220' and actuator 230' by any suitable method, e.g., by adhesive, sonic welding, etc. Alternatively, mechanism 242' might be formed as a whole in a single molding operation.

Figure 10A:
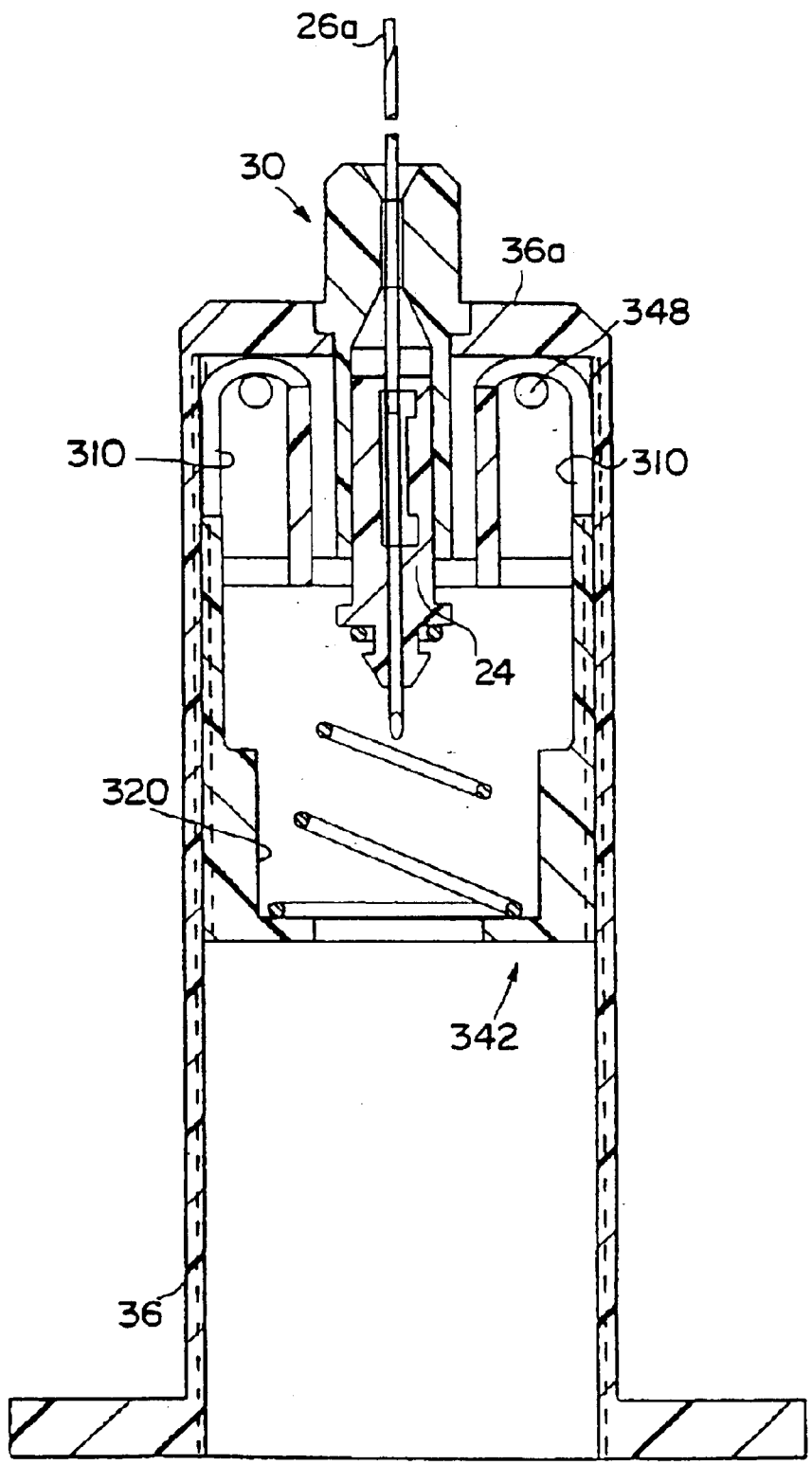
FIGS. 10A and 10B are schematic cross-sectional views of a blood collection needle in accordance with still another embodiment of the present invention.
Figure 10B:
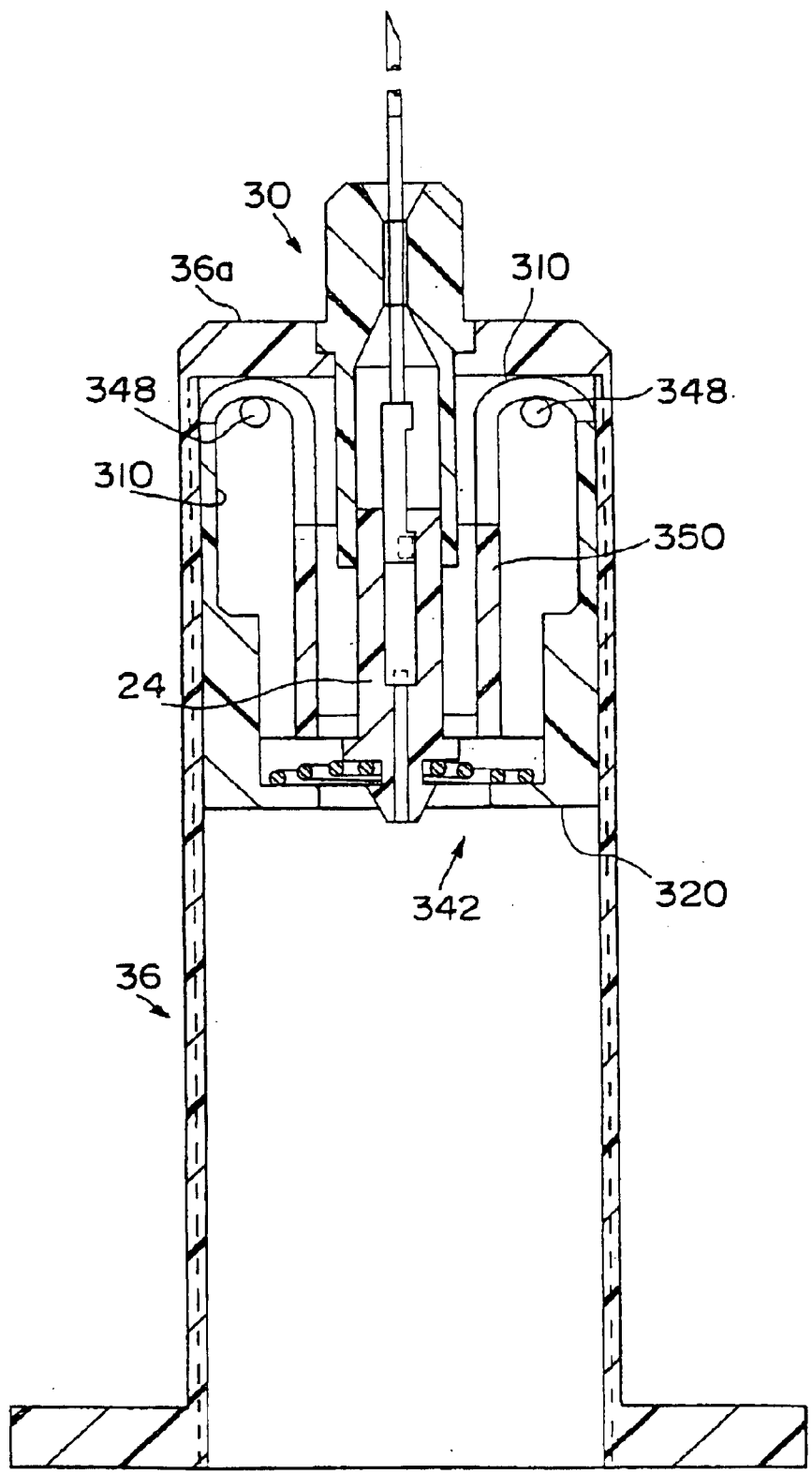

According to yet another embodiment of the invention, a mechanism 342 shown in FIG. 10A comprises pliable, resilient straps 310 connecting a transmitting sleeve 320 and an actuator ferrule 350. Straps 310 are configured to have a reverse bend about pins 348, and so extend forward from the forward edge of transmitting sleeve 320, around pins 348 to actuator ferrule 350, from which it extends forward as well. In the region of the reverse bend around pins 348, straps 310 may slidably bear against the interior of forward end 36a of holder 36. FIG. 10A shows the device in a blunted configuration corresponding to the configuration shown in FIG. 4B. When a collection tube is inserted into holder 36, transmitting sleeve 320 is moved forward in holder 36, pushing straps 310 against the forward end 36a of holder 36. Straps 310 loop around pins 348 and push actuator ferrule 350 rearward, unlocking needle assembly 30 and pulling shuttle 24 to a retracted position as shown in FIG. 10B, placing the device in a sharpened configuration. Thus, straps 310 constitute a reversing link between the transmitting sleeve 320 and the actuator ferrule 350, performing an equivalent function to the gear and toothed splines of the embodiment of FIG. 3.

In each of the foregoing embodiments, the transmitter is movable axially, i.e., longitudinally, in the shell, and it is not fastened to the shell. According to other embodiments of this invention, however, the transmitter device may move directly or indirectly to and fro relative to the central axis of the shell, thus moving obliquely relative to the motion of a sample collection tube being inserted into, or withdrawn from, the shell. Such radial motion is also oblique relative to the axial forward and rearward motions of the actuator. In contrast to previously described embodiments, the transmitter device may optionally be fastened to the shell, since no substantial axial movement is required of it. In such embodiments, the transmitter device may comprise at least one, preferably at least two, resilient arms secured to the interior of the holder. The transmitter device, i.e., one or more transmitter arms, is configured so that when a collection tube is inserted into the holder, the tube bears against it and presses it sideways towards the shell of the holder. Thus, the transmitter device moves obliquely relative to the collection tube. A linkage between the transmitter device and the actuator, such as a cam and follower engagement between them, converts the oblique (sideways) motion of the transmitter device into forward or rearward motion of the actuator. Thus, the transmitter device moves obliquely relative to the actuator. As with the previously described embodiments, the motion of the actuator (and of the blunting member, when one is secured thereto) is opposite to that of the sample collection tube. One example of such an embodiment is shown in the accompanying FIG. 11, in which a blood collection needle 455 comprises a holder 436 in accordance with the present invention. Holder 436 comprises a cylindrical shell 438 which has a front end 436a and a back end 436b and a mechanism 442 therein, described below. At front end 436a, shell 438 defines a needle hub 410 in which a needle cannula 422 is mounted. Back end 436b and shell 438 are dimensioned and configured to receive a sample collection tube therein.

In a blunting mechanism 442, the transmitter device comprises a set of resilient transmitting arms 444a which are mounted in the interior of shell 438 and which extend forwardly in the interior of the shell. Transmitting arms 444a also extend towards the central axis of the shell so that when a sample collection tube is inserted in the back end of holder 436, it bears against transmitting arms 444a. Transmitting arms 444a, being flexible and resilient, are displaced from the central region of shell 438 towards the wall of the shell as the sample collection tube moves forward in holder 436, and transmitting arms 444a move inwardly as the sample collection tube is withdrawn, i.e., the arms move obliquely (i.e., radially) relative to the generally axial motion of the sample collection tube. In the illustrated embodiment, transmitting arms 444a are fastened to the shell near the back end of the shell and extend forwardly therein (in other embodiments, they might extend rearwardly from the front). Each of transmitting arms 444a carries a wedge 446a which points outwardly, towards shell 438, and each wedge has a cam surface S.

Blunting mechanism 442 also comprises a ferrule-shaped actuator 450 disposed within shell 438. Actuator 450 is dimensioned and configured to receive therein the transmitting arms 444a. Actuator 450 comprises a cannula hub 451 which engages a second cannula 426 which extends forwardly therefrom and is disposed concentrically within needle cannula 422. The forward-extending portion of cannula 426 terminates with a blunt end and constitutes the blunting member 426a of the device. Cannula 426 also extends rearward, terminating at a sharp end for puncturing the seal on a sample collection tube and for providing a conduit for fluid flow between the sample collection tube in holder 436 and needle cannula 422. The sharp end of cannula 426 is covered with a self-resealing boot 427 which blocks fluid flow from the tip end of cannula 426 until the boot is displaced by a collection tube. The boot re-seals cannula 426 when the collection tube is removed, as is known in the art. Cannula 426 is secured to actuator 450 so that it moves with actuator 450. A spiral spring 454 is positioned within shell 438 to urge actuator 450 forward and serves as a biasing member in this embodiment. Other biasing members, e.g., other types of springs, an elastic band, etc., may be used as a biasing means in place of spring 454. Since the annular portion of actuator 450 extends rearward from hub 451, it is configured to seat the end of a sample collection tube and permit the blunting cannula to perforate the seal on the collection tube.

Needle cannula 422, second cannula 426, actuator 450, transmitter arms 444a and shell 438 are dimensioned and configured so that when actuator 450 is in its forward-most position within shell 438, blunting member 426a extends beyond the sharp tip of needle cannula 422, thus blunting the device, i.e., the device is in a blunted configuration. They are further configured so that when actuator 450 is moved rearward under the operation of mechanism 442, the blunt end of blunting member 426a is withdrawn into needle cannula 426, thus exposing the sharp tip of the needle and placing the device in a sharpened configuration, as follows. Actuator 450 is equipped with wedge apertures 452. Arms 444a and wedges 446a are configured so that when a sample tube is inserted into holder 436, the tube bears against arms 444a, pushing them outward so that surfaces S engage the rearward interior edge of wedge apertures 452. As the sample collection tube moves arms 444a still farther apart from one another, wedges 446a are driven farther outward and actuator 450 rides along surfaces S and is thus moved backward in the device. Thus, surfaces S serve as cam surfaces and actuator 450 serves as a cam follower.

In this embodiment, arms 444a are configured so that the sample collection tube contacts arms 444a at a point between their connection to shell 438 and their linkage to actuator 450. The arms 444a flex about their points of attachment to shell 438, which serve as their fulcrums. It may be noted that the arms 444a move in response to a force applied by the sample tube between the fulcrum and the load (actuator 450), so arms 444a act as levers of the third class. If necessary, shell 438 may comprise shell apertures 438a to accommodate the protrusion of wedges 446a entirely through wedge apertures 452. When actuator 450 begins in its forward-most position (the blunting position) and is then moved rearward by arms 444a and wedges 446a, blunting member 426a is withdrawn from its blunting position towards a position within needle cannula 422 (the sharpened position), thus sharpening the device. Arms 444a may be configured to cause actuator 450 to fully withdraw blunting member 426a into needle cannula 422, which is typically achieved with a travel of about 0.2 inch. Upon withdrawal of the sample collection tube from the holder, the resilience of arms 444a causes them to return towards the central region in shell 438, and surfaces S then permit actuator 450 to advance under the impetus of spring 454. In an alternative embodiment, a positive motion cam may be established between arms 444*a* and actuator 450 and the spring-like arms 444*a* may comprise the biasing means due to their resiliency to advance the actuator 450 when arms 444*a* resume their inwardly-disposed configuration.

In another embodiment of the invention, the full withdrawal of blunting member 426*a* is accomplished in a staged manner by a plurality of sets of wedges. In such an embodiment, a holder 436, shown in FIGS. 12A, 12B and 12C, comprises a transmitter device comprising a first set of arms 444*b* with wedges 446*b* which may be configured to withdraw the actuator 450' and a blunting member (not shown) only part way, e.g., 0.1 inch. The transmitter device further comprises a second set of arms 444*c* and wedges 446*c*, and an actuator 450' and shell 438' which comprise apertures to accommodate both sets of wedges in a manner similar to that shown in FIG. 11. In such an embodiment, however, the second set of wedges 446*c* may be situated at a different point on the front-to-back length of shell 438 than the first set of wedges 446*b*. Thus, the mechanical action of the two sets of wedges is staggered. Each set may separately accomplish a part, e.g., approximately half, of the withdrawal motion to move blunting member 426*a* from its extended, blunting position to its withdrawn, sharpened position, over different (although possibly overlapping) time intervals from the other set of wedges as the sample collection tube is inserted into the holder. Thus, arms 444*b* in shell 438' are configured for the first contact with a sample collection tube and wedges 446*b* thereon are configured to effect a first portion of the rearward motion of actuator 450' by engaging apertures 438*b*. Arms 444*c* are configured for contact with the sample collection tube after arms 444*b*, and wedges 446*c* thereon are configured to effect the completion of the rearward motion of actuator 450' by engaging apertures 438*c* to sharpen the device. FIG. 12C provides an end view in which both sets of arms 444*b* and 444*c* are visible.

Figure 11:
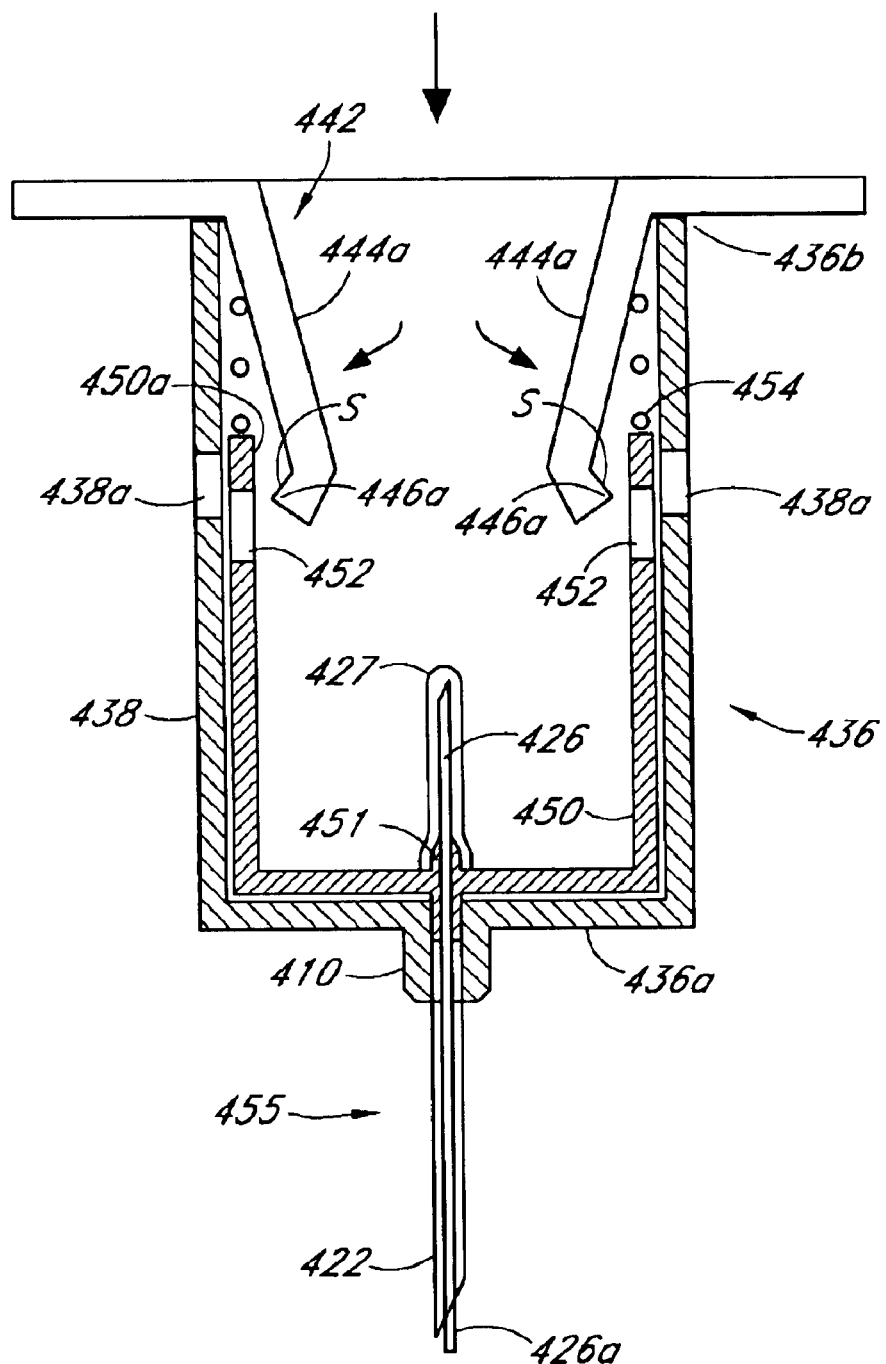
FIG. 11 is a schematic cross-sectional view of a blood collection needle comprising a needle holder in accordance with another lever embodiment of the present invention.

To provide a blood collection device of the present invention in an initially sharpened state prior to the first insertion of a sample collection tube, the transmitter arms can be extended beyond the wedges to include locking detents to retain the actuator in the withdrawn position prior to the first insertion of a sample collection tube into the device. For example, holder 436" of FIG. 13A comprises arms 444*d* which carry wedges 446*d* for engaging wedge apertures 52*e*. Arms 444*d* carry locking extensions 444*e* which terminate in locking detents 446*b*. Actuator 450" is provided with corresponding locking apertures 450*f* configured so that when actuator 450" is in an initial, rearward position, locking tabs 446*b* engage the front surface of actuator 450" via locking apertures 450*f*, as seen in FIG. 13B. Thus, the device may be disposed in an initial sharpened configuration even without a sample collection tube therein. Locking apertures 450*f* are dimensioned to permit arms 444*d* to move outwardly (i.e., radially relative to the central axis of shell 438, with which cannula 426 is aligned) and thus disengage tabs 446*b* from the actuator. Arms 444*a* are configured so that upon the initial insertion of a sample collection tube into shell 438, the arms are moved apart sufficiently to disengage locking tabs 446*b* from actuator 450" as indicated by arrows 453. Actuator 450" is then free to move forward under the pressure of a spring (not shown) like spring 454 (FIG. 11). As the sample tube is inserted further, however, the mechanism in the holder causes actuator 450" to move rearward again. The sample tube spreads arms 444*d* so that they pass through apertures 450*f* as actuator 450" moves rearward to a retracted position to sharpen the device. When the sample tube is withdrawn, actuator 450" moves forward, but the sample tube prevents tabs 446*b* from engaging the notches in apertures 450*f*. Instead, actuator 450" moves forward beyond the notches and beyond the ends of extensions 444*e*. Finally, arms 444 can move towards the center of the device and actuator 450" is fully advanced so that the blunting member blunts the needle cannula. The ends of arms 444 can then move toward the center of the shell into position to bear against the central portion of the actuator, as shown in FIG. 13C, and prevent actuator 450" from moving rearward, thus locking the device in the blunted configuration. When another sample collection tube is inserted into the device, arm extensions 444*e* will be driven outward so that they align with apertures 450*f* and they will thus permit the mechanism to move the blunting member rearward to sharpen the device. It will therefore be understood that tabs 446*b* only hold actuator 450" in the forward position in an initial configuration prior to the first insertion of a sample collection tube into the needle.

Figure 13A:
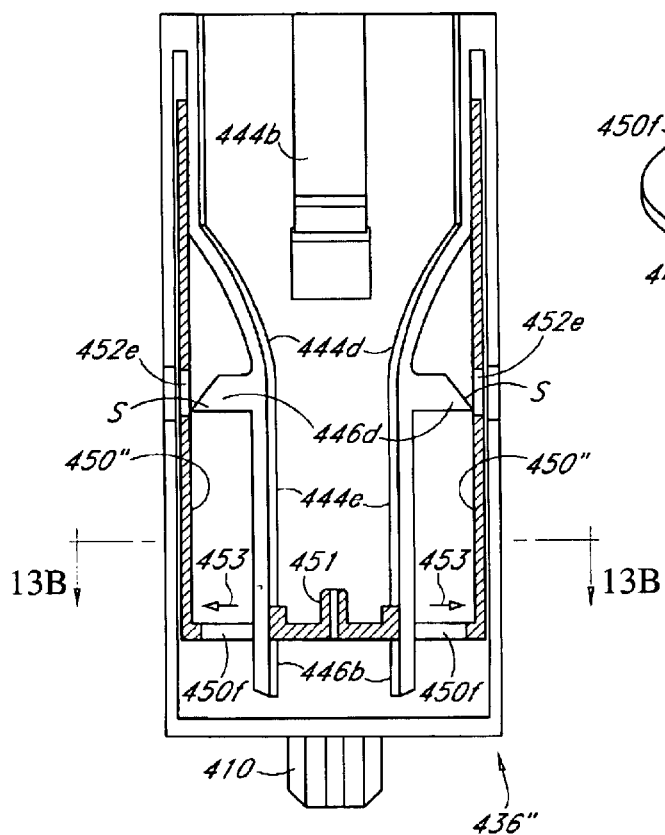
FIG. 13A is a cross-sectional view of a holder according to yet another embodiment of the invention.
Figure 13B:
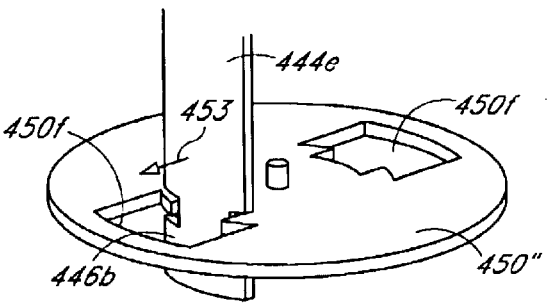
FIG. 13B is a partial perspective view of an arm extension and actuator of FIG. 13A shown in an initial, blunted configuration without a sample tube in the device.
Figure 13C:
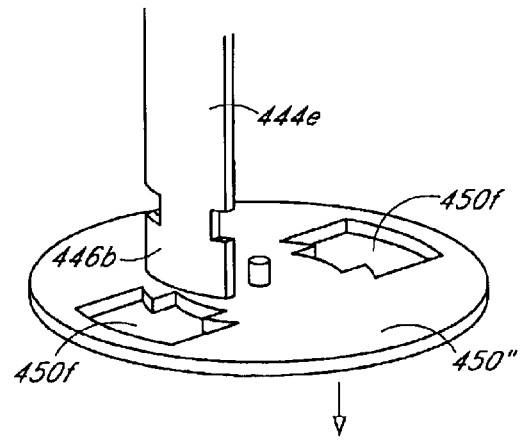
FIG. 13C is a view of the structures of FIG. 13B locked in a blunted position after the withdrawal of a sample tube from the device.

In use, a blood collection needle comprising holder 436" is initially provided in an initial sharpened configuration in which actuator 450" and a second (blunting) cannula (not shown) are withdrawn to the sharpened position and actuator 450" is engaged by locking tabs 446*b* (FIGS. 13A and 13B). In this initial sharpened configuration, the user can effect venipuncture with the needle cannula (not shown) in hub 410 and with the cannula boot (not shown) preventing fluid flow. Then, upon the initial insertion of a sample collection tube into holder 436", arms 444*d* move apart sufficiently to disengage locking tabs 446*b* from actuator 450" (as suggested by arrows 453). A spring (not shown) then urges actuator 450" forward, temporarily blunting the device. Upon further insertion of the sample collection tube, the cam surfaces S of wedges 446*d* engage apertures 452*e*, thus moving actuator 450" and the blunting member secured thereto rearward so that the needle is sharpened as the sample collection tube is fully inserted into the device. At the same time, the boot 427 is pushed past the sharp end of cannula 426 as the cannula pierces the seal on the collection tube to allow fluid flow into the tube. Actuator 450" is not retained in this position by locking tabs 446*b* because arms 444*d* are held apart by the sample tube and so cannot engage locking apertures 450*f*. Therefore, upon removal of the sample collection tube, actuator 450" moves forward again to the blunting position as wedges 446*a* withdraw from apertures 450*f*. By the time the sample collection tube is withdrawn, arms 444*d* have been withdrawn from apertures 450*f* and they are behind the central portion of actuator 450", locking the device in the blunted configuration until another sample collection tube is inserted into the device.

Figure 14C:
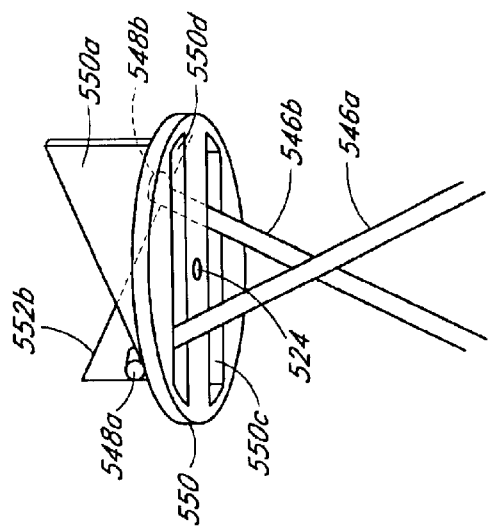
FIG. 14C is a perspective view of the transmitter arms and actuator of the mechanism shown in FIG. 14A.
Figure 14B:
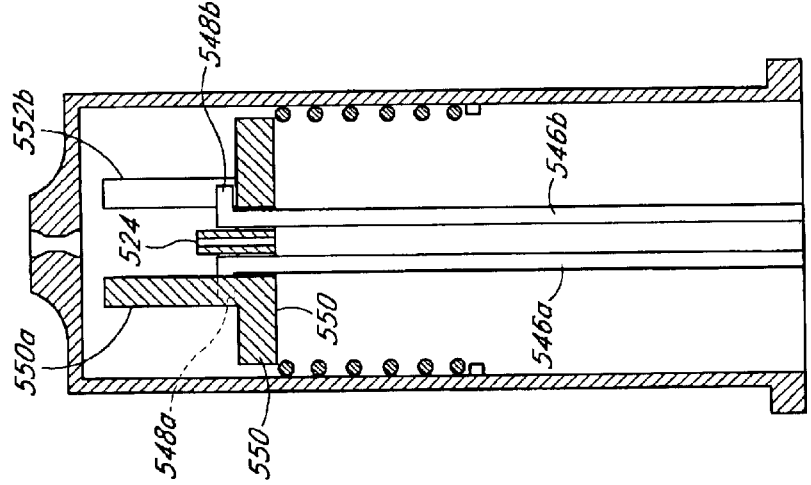
FIG. 14B is a view of the holder of FIG. 14A taken generally along the line indicated at B—B in FIG. 14A.
Figure 14A:
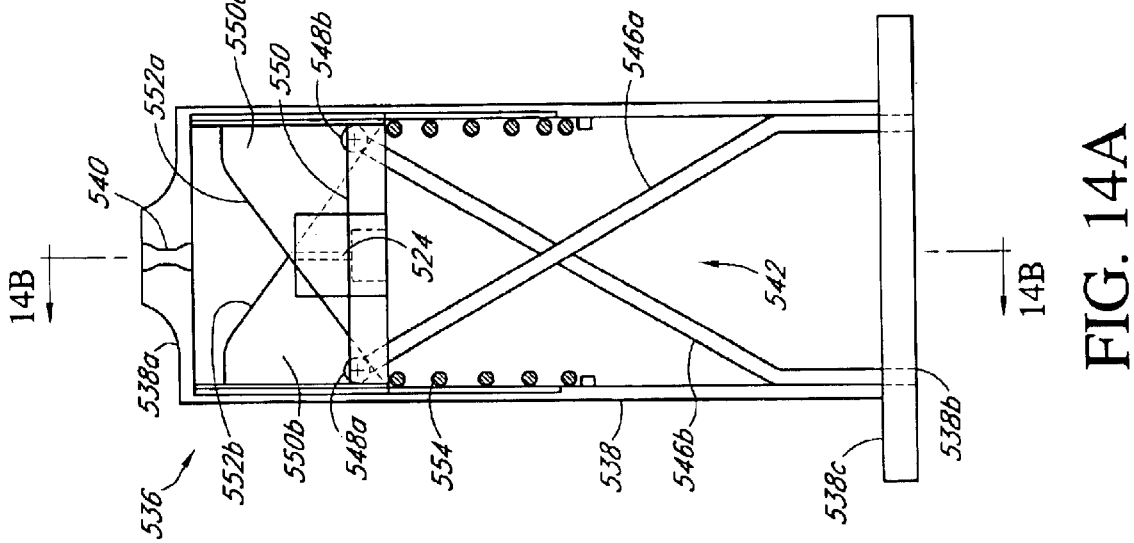
FIG. 14A is a schematic view of a needle holder in accordance with still another embodiment of the invention.
Figure 15:
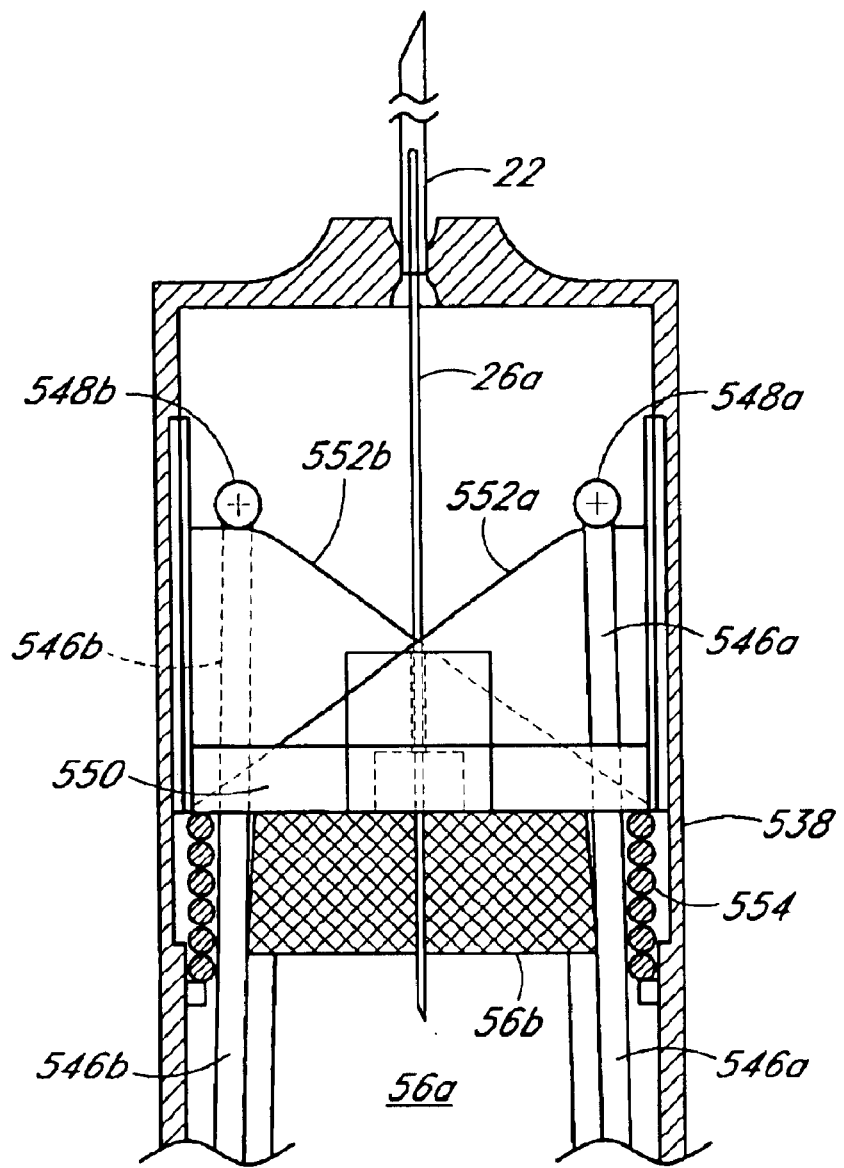
FIG. 15 is a schematic view of the holder of FIG. 14A with a needle, blunting member and sample collection tube therein, and with the device in the sharpened configuration.

Still another embodiment in accordance with the present invention is shown in FIGS. 14A through 15. In this embodiment, the transmitter device comprises two transmitter arms, each attached to one side of the interior of the holder and extending towards the other side. The transmitter arms terminate in lugs which ride on cam surfaces formed on the actuator. When a collection tube is inserted into the holder, the traversing sections of the transmitter arms are moved by the collection tube so that the lugs bear on the cam surfaces, thus moving the actuator. In particular, FIG. 14A shows a holder 536 for a blood collection needle comprising a shell 538 which has a generally cylindrical configuration with a front end 538*a* in which is formed a needle aperture 540 within which the needle may be mounted. Optionally, needle aperture 540 may be configured in the same manner as the mounting portion 14a of needle hub 10 (FIG. 1A), which has funnel-like insertion regions to facilitate the insertion of the needle therein and of the blunting member into the needle cannula. At the back end 538b, shell 538 comprises a finger flange 538c for the convenience of the user. Within shell 538, mechanism 542 effects rearward motion of a blunting member (to sharpen the device) in response to the insertion of a sample collection tube in the device. Mechanism 542 comprises transmitter arms 546a, 546b, actuator 550 and spring 554. Transmitter arm 546b is attached to shell 538 at the back end thereof and extends in a forward direction and generally traverses the central, interior portion of the shell (from left to right as sensed in FIG. 14A) to terminate at lug 548b. Transmitter arm 546a is configured similarly to arm 546b, but it is attached on the shell at a point generally opposite from where arm 546b is attached and it traverses the central portion of shell 538 in the opposite direction, as suggested in FIG. 14A. Actuator 550 carries a mounting lug in which a mounting aperture 524 is formed for receiving a blunting member. Actuator 550 also carries wedges 550a, 550b, each of which forms a cam surface 552a, 552b, respectively. Lug 548a is positioned to bear against cam surface 552a and lug 548b is positioned to bear against cam surface 552b. In the configuration shown in FIGS. 14A and 14B, actuator 550 is in the forwardmost position under the bias of spring 554, with lugs 548a and 548b at their lowest points on their respective cam surfaces 552a, 552b. In the view of FIG. 14B, it can be understood that while arms 546a and 546b appear to cross each other at about the center of shell 538, they also extend in planes that are generally parallel to one another. In the view of FIG. 14B, cam surface 552a is sloping downward into the foreground of the Figure but cam surface 552b faces away from the viewer and is not visible in that Figure. By comparing the views of FIGS. 14B and 14C, it will be understood that actuator 550 defines a pair of generally parallel slots 550c and 550d which straddle aperture 524 and that wedges 550a and 550b are formed alongside the slots. Slots 550c and 550d admit arms 546a and 546b therethrough to allow lugs 548a to rest on cam surface 552a and lug 548b to rest on cam surface 552b. The comparison of these Figures will also make clear that in the view of FIGS. 14B and 14C, cam surface 552b is inclined away from the viewer, and so is not visible in these Figures.

Referring again to FIG. 14a, it can be understood that when a sample collection tube is inserted into holder 536, it will bear against the mid-portions of transmitter arms 546a and 546b, between where arms 546a and 546b are attached to shell 538 and where they engage actuator 550, and bend them towards the sides of shell 538 to which they are attached. Lugs 548a and 548b will then bear against cam surfaces 552a and 552b, thus moving actuator 550 rearward (downward as sensed in FIGS. 14A and 14B) against the bias of spring 554. The result of such an arrangement is shown in FIG. 15, in which the insertion of sample collection tube 56a has substantially straightened transmitter arms 546a and 546b so that they no longer traverse the central portion of the shell 538. Lugs 548a and 548b rest at the top of cam surfaces 552a and 552b, respectively and have driven actuator 550 rearward, thus compressing spring 554. The blunting member 26a carried on actuator 550 is moved rearward in the device to the blunting configuration, leaving the tip of needle 26 exposed. Withdrawal of collection tube 56a will permit arms 546a and 546b to return to their crosswise configuration, thus allowing spring 554 to move actuator 550 forward, advancing blunting member 26a so that it protrudes from needle 22, thus blunting the device.

Optionally, any of the embodiments of FIGS. 11–15 may easily be configured to receive a removable needle and blunting member assembly of the kind shown in U.S. Pat. No. 5,951,520, the disclosure of which is hereby incorporated herein by reference.

While the invention has been described in detail with reference to particular embodiments thereof, it will be apparent that upon a reading and understanding of the foregoing, numerous alterations to the described embodiments will occur to those skilled in the art and it is intended to include such alterations within the scope of the appended claims.

What is claimed is:

1. A needle holder apparatus comprising:
   a shell dimensioned and configured for receiving and holding a sample collection tube therein and for carrying thereon a needle cannula; and an actuator movably disposed in the shell for engaging and moving a blunting member longitudinally within the shell, and means for moving the actuator axially between a forward position and a retracted position in response to the insertion and withdrawal of a sample collection tube in the shell.

2. The apparatus of claim 1 wherein the means for moving the actuator comprises a transmitter device connected to the shell and being configured to move obliquely in the shell upon insertion of such sample collection tube into the shell;
   a linkage between the transmitter device and the actuator to convert the oblique motion of the transmitter device into rearward motion of the actuator, when such sample tube is inserted into the apparatus; and a biasing member positioned and configured to urge the actuator toward the forward position.

3. The apparatus of claim 2 wherein the linkage comprises a cam and follower engagement between the actuator and the transmitter device.

4. The apparatus of claim 2 wherein the transmitter device is configured to contact such sample collection tube at a point between the connection to the shell and the linkage to the actuator.

5. The apparatus of claim 2 wherein the transmitter device extends forwardly in the shell from its point of attachment to the shell.

6. The apparatus of claim 2 wherein the transmitter device comprises at least two transmitter arms.

7. The apparatus of claim 2 comprising a staggered cam and follower engagement between the transmitter device and the actuator.

8. The apparatus of claim 3 wherein the actuator comprises at least one cam surface.

9. The apparatus of claim 3 wherein the transmitter device comprises at least one cam surface.

10. A needle holder apparatus comprising:
    a shell dimensioned and configured for receiving and holding a sample collection tube therein and for carrying thereon a needle cannula;
    an actuator movably disposed in the shell for engaging and moving a blunting member axially within the shell;
    a transmitter device connected to the shell and being configured to contact a sample collection tube which may be inserted into the shell and to move obliquely relative to the motion of the sample collection tube; and a positive motion cam engagement between the transmitter device and the actuator to convert the oblique motion of the transmitter device into axial motion of the actuator, wherein the apparatus is biased to dispose the actuator in the forward position.

11. A blood collection needle comprising:

a shell dimensioned and configured for receiving and holding a sample collection tube therein;

a needle cannula carried on the shell;

a blunting member disposed telescopically within the needle cannula for movement between a withdrawn position which disposes the needle in a sharpened configuration and a blunting position which disposes the needle in a blunted configuration; and a mechanism for moving the blunting member to the withdrawn position when a sample collection tube is inserted into the holder and for moving the blunting member to the blunting position when the sample collection tube is withdrawn from the shell.

12. A blood collection needle comprising:

a shell dimensioned and configured for receiving and holding a sample collection tube therein;

a needle cannula carried on the shell;

a blunting member disposed telescopically within the needle cannula for movement between a withdrawn position which disposes the needle in a sharpened configuration and a blunting position which disposes the needle in a blunted configuration;

an actuator movably disposed in the shell, the actuator being secured to the blunting member so that the blunting member can be moved axially between the blunting position and the withdrawn position by movement of the actuator;

a movable transmitter device connected to the shell and being configured for contact with a sample collection tube which may be inserted into the shell, the transmitter device being configured to move obliquely relative to the motion of a sample collection tube in the shell;

a biasing member positioned and configured to urge the blunting member to the blunting position upon withdrawal of such sample collection tube from the shell; and a linkage between the transmitter device and the actuator to convert the oblique motion of the transmitter device into rearward motion of the actuator, to move the blunting member at least from the blunting position to the withdrawn position.

13. The needle of claim 12 wherein the linkage comprises a cam and follower engagement between the transmitter device and the actuator.

14. The needle of claim 12 or claim 13 wherein the transmitter device is configured to contact such sample collection tube at a point between the connection to the shell and the linkage to the actuator.

15. The needle of claim 13 wherein the actuator comprises at least one cam surface.

16. The needle of claim 13 wherein the transmitter device comprises at least one cam surface.

17. The needle of claim 13 comprising a staggered cam and follower engagement between the transmitter device and the actuator.

* * * * *

UNITED STATES PATENT AND TRADEMARK OFFICE
CERTIFICATE OF CORRECTION

PATENT NO.     : 6,733,465 B1  
DATED          : May 11, 2004  
INVENTOR(S)    : Smutney et al.

It is certified that error appears in the above-identified patent and that said Letters Patent is hereby corrected as shown below:

<u>Title page,</u>
Item [75], Inventors, delete "Newington" and insert -- Vernon --.
Item [56], References Cited, FOREIGN PATENT DOCUMENTS, after "10/1958" insert -- A61m --.

Signed and Sealed this

Thirteenth Day of June, 2006

JON W. DUDAS
*Director of the United States Patent and Trademark Office*